US012670972B2

(12) United States Patent
Hafen et al.

(10) Patent No.: US 12,670,972 B2
(45) Date of Patent: Jun. 30, 2026

(54) ADAPTIVE CLINICAL TRIAL DATA ANALYSIS USING AI-GUIDED VISUALIZATION SELECTION

(71) Applicant: Telperian, Inc., Austin, TX (US)

(72) Inventors: Ryan Hafen, Austin, TX (US); Brian Hobbs, Austin, TX (US); Michael Kane, Austin, TX (US)

(73) Assignee: Telperian, Inc., Austin, TX (US)

( * ) Notice: Subject to any disclaimer, the term of this patent is extended or adjusted under 35 U.S.C. 154(b) by 16 days.

(21) Appl. No.: 19/048,638

(22) Filed: Feb. 7, 2025

(65) Prior Publication Data

US 2025/0253016 A1 Aug. 7, 2025

Related U.S. Application Data

(60) Provisional application No. 63/550,743, filed on Feb. 7, 2024.

(51) Int. Cl.
G16H 10/20 (2018.01)
G06F 16/248 (2019.01)
(Continued)

(52) U.S. Cl.
CPC ........... G16H 10/20 (2018.01); G06F 16/248 (2019.01); G16H 10/60 (2018.01); G16H 50/70 (2018.01)

(58) Field of Classification Search
CPC ........ G16H 10/20; G16H 10/60; G16H 50/70; G06F 16/248
See application file for complete search history.

(56) References Cited

U.S. PATENT DOCUMENTS 10,152,512 B2 * 12/2018 Cohen ....................... G06F 8/30
10,339,653 B2 7/2019 Gillies et al.
(Continued)

FOREIGN PATENT DOCUMENTS

WO WO-2010059691 A1 * 5/2010 ......... G06F 16/2365

OTHER PUBLICATIONS

Tao S, Cui L, Wu X, Zhang GQ. Facilitating Cohort Discovery by Enhancing Ontology Exploration, Query Management and Query Sharing for Large Clinical Data Repositories. AMIA Annu Symp Proc. Apr. 16, 2018;2017:1685-1694. (Year: 2017).*
(Continued)

*Primary Examiner* — Linh Giang Le
(74) *Attorney, Agent, or Firm* — Pillsbury Winthrop Shaw Pittman, LLP

(57) ABSTRACT

Provided is a method, including obtaining data associated with clinical trials, storing the obtained data into a repository by preprocessing the data to standardize diverse input formats into unified data model and organizing the stored data into a schema designed to integrate data of diverse input formats, indexing the stored data and analyses performed on the stored data, selecting one or more visualizations responsive to the query by selecting one or more visualizations as being responsive to the query based on metadata associated with each of the one or more visualizations, determining whether the stored data is associated with a plurality of metadata requirements of each of the one or more visualizations, dynamically generating executable code configured to generate the one or more visualizations responsive to the query, executing the generated executable code, and providing a response to the query.

38 Claims, 3 Drawing Sheets

(51) Int. Cl.
    *G16H 10/60*      (2018.01)
    *G16H 50/70*      (2018.01)

(56)            References Cited

U.S. PATENT DOCUMENTS

| | | |
|---|---|---|
| 10,860,635 B2 | 12/2020 | Bator et al. |
| 10,878,064 B2 | 12/2020 | Burns et al. |
| 10,963,821 B2 | 3/2021 | Barnes et al. |
| 11,769,114 B2 | 9/2023 | Saxena et al. |
| 2012/0078521 A1 | 3/2012 | Avinash et al. |
| 2018/0122497 A1 | 5/2018 | Pietronigro et al. |
| 2024/0203564 A1 | 6/2024 | Kamen et al. |

OTHER PUBLICATIONS

Hafen, Ryan, U.S. Appl. No. 18/990,773, titled "Representing Clinical Trial Data in an Interactive Analysis Platform," filed Dec. 20, 2024, 59 pages.

DeepSeek AI, et al., "DeepSeek-R1: Incentivizing Reasoning Capability in LLMs via Reinforcement Learning," Jan. 22, 2025, 22 pages [online], [retrieved on Feb. 10, 2025]. Retrived from the Internet <URL.: https://arxiv.org/pdf/2501.12948><arXiv:2501.12948v1>.

Web Archive of Telperian, Inc.'s Product Webpage, Nov. 30, 2023, 4 pages [online], [retrieved on Feb. 10, 2025]. Retrieved from the Internet: <URL: https://web.archive.org/web/20231130114835/https:/telperian.com/products/>.

* cited by examiner

ADAPTIVE CLINICAL TRIAL DATA ANALYSIS USING AI-GUIDED VISUALIZATION SELECTION

CROSS-REFERENCE TO RELATED APPLICATIONS

This patent claims the benefit of U.S. Provisional Patent Application 63/550,743, filed 7 Feb. 2024, titled SEARCHABLE AND NAVIGABLE ELECTRONIC SYSTEM FOR FINDING RESULTS FROM MANY ANALYSES APPLIED TO DATA. The entire content of each afore-listed earlier-filed application is hereby incorporated by reference for all purposes.

BACKGROUND

1. Field

The present disclosure relates generally to computer systems for managing data related to clinical studies and, more specifically, to a searchable and navigable electronic system for finding results from many analyses applied to clinical-trial data.

2. Description of the Related Art

A clinical trial is a structured research study designed to evaluate the safety, efficacy, and overall impact of a medical intervention, such as a drug, device, or treatment protocol, on human participants. Conducted in multiple phases, these trials assess how a treatment performs in controlled environments before being approved for widespread use. The data collected during a clinical trial includes demographic and baseline health information of participants, pharmacokinetic and pharmacodynamic responses, efficacy outcomes measuring the treatment's intended effects, and safety data capturing adverse events, toxicity levels, and potential side effects. Additional data points include biomarker analyses, laboratory test results, quality-of-life assessments, and patient-reported outcomes to understand broader implications of the intervention. Regulatory agencies, such as the United States Food and Drug Administration (FDA) or the European Medicines Agency (EMA), require detailed and well-structured clinical trial data to ensure that new treatments meet established safety and effectiveness standards before they reach the public.

SUMMARY

The following is a non-exhaustive listing of some aspects of the present techniques. These and other aspects are described in the following disclosure.

The following embodiments may be useful to address the challenges associated with analyzing, querying, and visualizing complex clinical trial data efficiently and accurately across diverse data formats and schemas. Some embodiments support interactive query processing, dynamic visualization generation, metadata-driven data analysis, and automated anomaly detection to enhance clinical trial workflows. While the described embodiments may be useful to address the challenges discussed above, it should not be assumed that all embodiments are designed to address these challenges but may be created to address other undescribed challenges or needs.

Some aspects include a method including: obtaining, with a computer system, data associated with clinical trials, wherein the data is sourced from a plurality of formats and modalities; storing, with the computer system, the obtained data into a repository by preprocessing the data to standardize diverse input formats into unified data model, and organizing the stored data into a schema designed to integrate data of diverse input formats, indexing, with the computer system, the stored data and analyses performed on the stored data, wherein indexing comprises associating metadata with each analysis, receiving, with the computer system, a query related to the stored data, selecting, with the computer system, one or more visualizations responsive to the query by selecting one or more visualizations as being responsive to the query based on metadata associated with each of the one or more visualizations, determining whether the stored data is associated with a plurality of metadata requirements of each of the one or more visualizations, dynamically generating executable code configured to generate the one or more visualizations responsive to the query, wherein the executable code is generated based on the query, metadata associated with the visualizations, and mappings between the metadata associated with the visualizations and the stored data, and executing the generated executable code, and providing, with the computer system, a response to the query, the response including the selected one or more visualizations.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
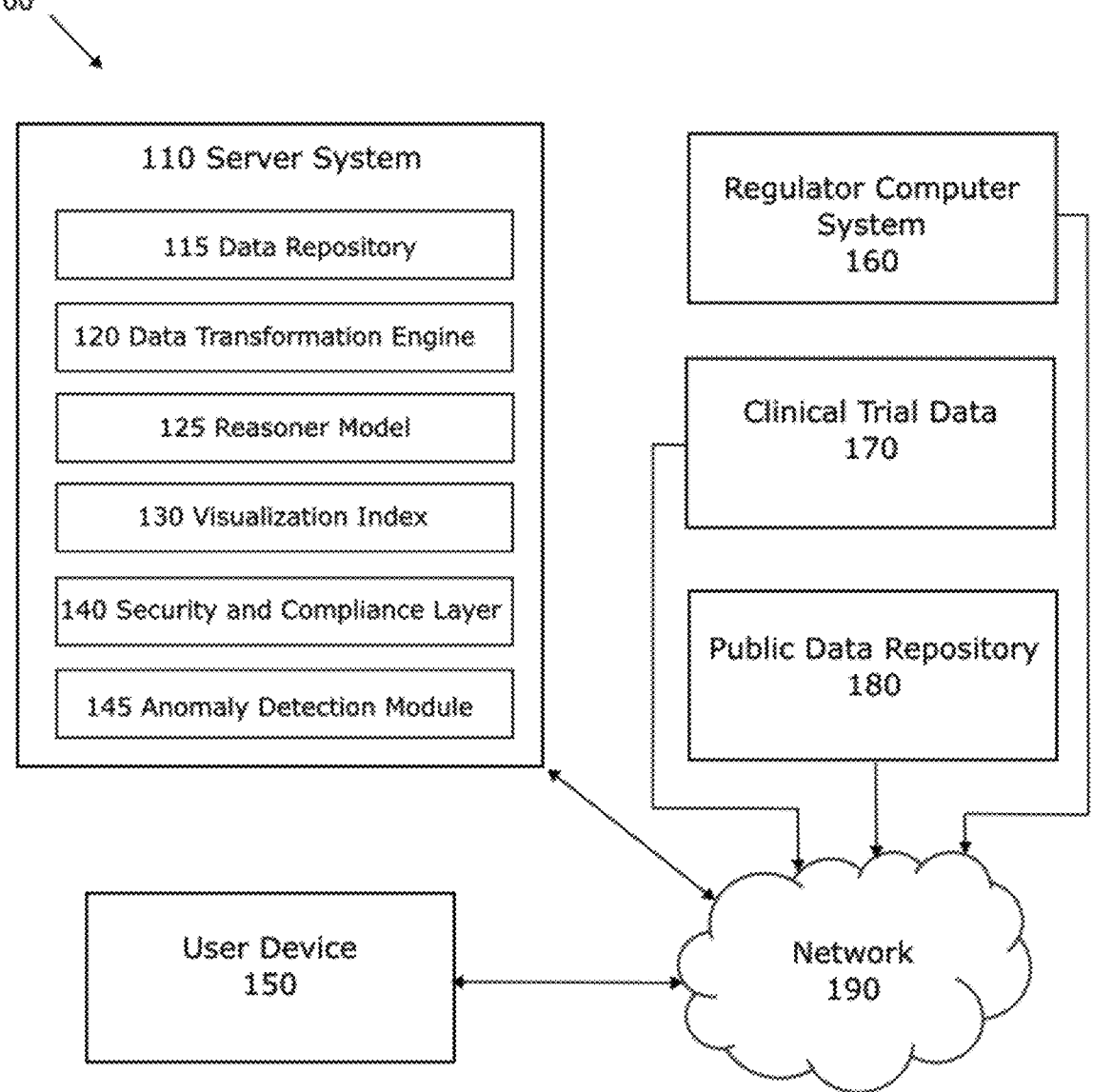
FIG. 1 illustrates an exemplary system architecture for dynamically generating visualizations and analyses based on clinical trial data.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of clinical data management and analysis. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

There are a variety of tools that can be used to explore clinical trial data. Examples include Clinical Trial Data Management and Analysis Platforms, like IBM Watson™ for Clinical Trial Matching, Medidata Rave & SAS Clinical Trial Analytics™, and Oracle Health Sciences Clinical One Analytics™; AI-Assisted Data Exploration Tools, like Tableau™, Microsoft Power BI with AI Insights™, and Google Looker™; and AI-Driven Automated Statistical Analysis Systems, like AutoStat™, DataRobot AutoML™ and various forms of AI-Driven Hypothesis Testing (e.g., Google DeepMind AlphaFold™ for bioinformatics).

Many existing data analytics platforms rely on predefined dashboards and require users to manually configure filters and select analyses, limiting their ability to dynamically surface insights. Many general-purpose AI-powered analytics tools often can process natural language queries but lack an understanding of clinical trial data structures, statistical reporting standards, and regulatory constraints, making them unsuitable for regulatory submissions. AI-driven statistical modeling tools often can automate analysis selection but do not provide direct mappings between statistical outputs and pre-validated regulatory visualizations. Additionally, many clinical data analytics systems do not offer an exploratory framework that identifies meaningful subpopulations or suggests new analytical pathways based on user input. Many query-based tools often require users to have prior knowledge of the data structure and available visualizations, rather than dynamically adapting to evolving queries and refining results iteratively. These limitations prevent existing solutions from delivering automated, domain-specific, and regulation-ready insights in clinical trial data analysis.

As a result, existing methods for querying and retrieving information from clinical datasets often require significant technical expertise. Ad-hoc analyses frequently rely on custom queries or scripts written by statisticians to extract relevant data points. This reliance on manual query development not only creates a substantial barrier for non-technical stakeholders, such as clinicians or regulatory reviewers, but also increases the risk of errors due to the inherent limitations of manual processes. The manual nature of these analyses leaves room for human error, oversight, and inconsistencies, particularly when querying large, complex datasets with multiple interdependencies. Critical patterns or trends in the data may go unnoticed due to time constraints and cognitive limitations, leading to missed opportunities for deriving actionable insights. The absence of intuitive, user-friendly tools for querying data compounds these challenges, slowing down the analysis process and impeding timely decision-making in clinical research and regulatory contexts.

Several technical challenges make it difficult for existing tools to effectively solve these problems associated with clinical trial data analysis. One issue is the nearly infinite number of ways to filter, group, and visualize clinical data, making it impractical to precompute and store all possible statistical outputs. Indeed, real-time analysis of large datasets, particularly those involving survival analysis, adverse event monitoring, and anomaly detection, can require computational efficiency that many conventional tools lack, in part due to this large number of permutations of different ways to analyze the data.

Some embodiments mitigate the issues associated with the nearly infinite number of ways to filter, group, and visualize clinical data by dynamically generating statistical outputs and visualizations on demand rather than precomputing and storing all possible results. Instead of relying on static reports or predefined queries, the system, in some embodiments, leverages a structured metadata model that describes available datasets, statistical methods, and visualization types, allowing it to intelligently determine which analyses are relevant to a given user query. By incorporating a large language model (LLM) trained on clinical data structures, regulatory requirements, and statistical methodologies, the system can interpret natural language inputs and automatically traverse a tree of possible outputs to identify the most appropriate visualization or statistical test, thereby narrowing the search space with domain-specific heuristics in some cases. Some embodiments further mitigate this issue by supporting iterative refinement, where users can refine queries dynamically, allowing real-time adjustments to filters, groupings, and statistical parameters without requiring a new manual analysis each time.

Another technical challenge is that the need for regulatory compliance, in some cases, can impose additional constraints, as those specifying outputs must be clinically validated and interpretable, preventing the end-to-end use of purely black-box AI models. Many existing tools are considered black-box models because they rely on complex machine learning algorithms, such as deep neural networks or ensemble methods, that do not provide clear, interpretable explanations of how they arrive at their conclusions, which is not to suggest that such approaches are disclaimed or disavowed.

Some embodiments may address the requirement, in some use cases, that outputs must be clinically validated and interpretable by integrating AI-driven assistance within a structured, rules-based framework rather than relying only on purely black-box AI models. Instead of allowing an opaque machine learning model to generate results without oversight, some embodiments use a metadata-driven approach that explicitly maps datasets, statistical methods, and visualizations to predefined, clinically validated outputs. Each statistical analysis and visualization recommended by the system, in some embodiments, may be drawn from a curated set of analysis types that have been pre-approved for regulatory use, helping ensure, in some embodiments, that generated insights adhere to established clinical and statistical standards. For example, regulatory compliance may be enforced, in some embodiments, by constraining visualization and statistical selections to those that align with industry best practices, such as Kaplan-Meier survival curves for time-to-event analyses or waterfall plots for efficacy assessments.

It should be understood that the described techniques are not limited to systems that fully address all the issues identified above. Instead, the techniques are generalizable to a wide range of problems and may address subsets of these challenges or other issues apparent to one skilled in the art.

In some embodiments, the disclosed system and methods may provide a framework for dynamically generating, analyzing, and interpreting clinical trial data through an intelligent query-driven visualization system. The system may be configured to ingest clinical trial data from various sources, including structured databases, semi-structured repositories, and unstructured records, standardizing the data into a unified schema. Metadata associated with the data may be indexed to support efficient querying and analysis, allowing users or automated systems to submit queries in natural language, Boolean expressions, or structured formats. The system may employ a reasoner model or alternative selection methodologies to determine appropriate visualizations in response to a given query. In some embodiments, visualization selection may be optimized using reinforcement learning models, where a policy model refines decision-making over time based on metadata alignment, user preferences, and relevance metrics. The system may dynamically generate executable code to construct the selected visualizations, with execution occurring in various environments, including the server system or distributed computing frameworks. Additionally, the system may integrate an anomaly detection module to identify inconsistencies in the clinical trial data, with issue tracking mechanisms providing traceability and resolution workflows. A large language model (LLM) may be utilized to interpret visualizations, providing users with summaries, insights, or contextual analysis, as well as identifying potential anomalies within the visualized data.

FIG. 1 is a block diagram that illustrates an exemplary system architecture 100 for generating visualizations and analyses based on clinical trial data. The system may include a server system 110, which may serve as a central processing hub and may be connected to various external components, either directly as shown, or via the network 190, such as the internet. These external components may include a public data repository 180, a clinical trial data repository 170, a regulator computer system 160, and a user device 150. Each of these components may be implemented with one or more of the computing devices described below with reference to FIG. 3. In some cases, any combination of these components may be integrated in the same computing system, or even the same computing device, e.g., as a monolithic application, or they may be distributed.

The user device 150 may execute a native application or a web application configured to access ingested clinical trial data and publicly available data stored within the server system 110. For example, the user device 150 may provide queries to the server system 110, which may be configured to analyze these queries and generate visualizations or analyses responsive to the user's input. The user device 150 may interact with the server system 110 to allow users to query, analyze, and visualize clinical trial data. In some embodiments, the user device 150 may submit queries to the server system 110 via a web-based or native application-based user interface.

Some embodiments may support interaction with a regulator computer system 160, which may verify that the server system 110 complies with various regulations. The regulator computer system 160 may represent a governmental or regulatory body, such as the FDA, and this computer system may host documents retrieved and used by the server system 110 for checking that the system 110 adheres to compliance requirements for clinical trial data handling and reporting. In some cases, such documents may be used in the below-described training operations as well as for verification at inference time.

Some embodiments may analyze data hosted in clinical trial data repository 170. Clinical trial data may be structured and stored in many different forms by different pharmaceutical companies. In some cases, the data arrives in the form of a case report form (CRF), which can be an electronic or paper document that records the protocol and information about each participant at different points of the study. Raw data may also be received from laboratory testing results and other sources in some cases. Electronic Data Capture (EDC) Systems and other tools may be used to help collect and manage the data of ongoing trials, but the way the raw data can be structured and stored varies greatly. These raw formats can be challenging to use for meaningful analysis and can entail a great deal of transformation to be useful for that purpose. As such, some embodiments may transform the data into a unified format, process the data, and host the data with techniques like those described in U.S. patent application Ser. No. 18/990,773, titled REPRESENTING CLINICAL TRIAL DATA IN AN INTERACTIVE ANALYSIS PLATFORM, filed Dec. 20, 2024 by the same Applicant, the contents of which are hereby incorporated by reference.

A case report form in a clinical trial may include fields designed to collect protocol-specified information related to a study participant. Subject identification and demographic details may be recorded, including a unique subject identifier, age, date of birth, sex, race, ethnicity, height, weight, and body mass index. Documentation of informed consent may be included, specifying the date of consent and the version of the informed consent form used. Medical history and baseline characteristics may be captured, such as pre-existing conditions, relevant medical history, prior and concomitant medications, and baseline laboratory values and vital signs. Information regarding study eligibility and enrollment may be documented, including an assessment of inclusion and exclusion criteria and randomization details when applicable. Treatment administration and compliance data may be recorded, including the date and time of investigational product administration, dose, route, frequency, and compliance assessment. Study visits and procedures may be detailed, with records of scheduled and completed visits, physical examinations, laboratory tests such as blood tests and urinalysis, and imaging or diagnostic assessments. Efficacy assessments may be included, capturing measurements related to primary and secondary endpoints as well as patient-reported outcomes when relevant. Safety and adverse event reporting may be documented, including adverse events and serious adverse events with information on severity, causality assessment, and outcome, along with laboratory abnormalities and unexpected findings. Concomitant medications and therapies may be recorded, tracking changes in medications during the study and any use of rescue medications. Protocol deviations may be noted, with documentation of any departures from the study protocol. Study completion or withdrawal information may be included, recording the date and reason for withdrawal or completion along with final assessments and follow-up details. The case report form is structured to ensure that data required for regulatory submissions and clinical analysis are systematically and consistently collected across study sites.

The obtained data may be derived from a plurality of formats and modalities, encompassing structured formats such as relational databases and CSV files, semi-structured formats such as JSON and XML, and unstructured formats such as free-text clinical notes, scanned documents, or multimedia files. Modalities may include numeric data, categorical data, textual data, time-series data, images such as radiological scans, or biometric data collected from wearable devices. Embodiments may obtain this data through various mechanisms, including secure APIs, batch uploads, or real-time streaming protocols, such as IoTenabled medical devices or cloud-based data streams. The system may also ingest historical data stored in legacy formats or capture live data directly from clinical trial sites using electronic case report forms (eCRFs).

The server system 110 may include various modules that may function to provide analyses and visualizations to users like those described above. Such modules may include a data repository 115, a data transformation engine 120, a reasoner model 125, a visualization index 130, a security and compliance layer 140, and an anomaly detection module 145.

In some cases, the data repository 115 may store clinical trial data ingested by the server system 110, e.g., from repository 170. This local repository 115 may store diverse datasets, including patient records, laboratory results, adverse events, and pharmacokinetic data, in a structured format, e.g., with data like that described above associated with the repository 170. In some embodiments, the data repository 115 may maintain metadata describing the origin, transformation history, and schema of each dataset, supporting efficient query execution and traceability. In some embodiments, the system 110 may integrate with, and ingest data for clinical trial records, from various types of external data sources, such as wearable devices, electronic health records (EHRs), or health claims databases.

The data transformation engine 120 may interface with the data repository 115 to preprocess raw clinical trial data, converting it into a unified data model that conforms to a predefined schema, such as the above-described unified format. This preprocessing may include standardization, normalization, and imputation of missing values. For instance, the data transformation engine 120 may convert demographic data from varying formats (e.g., CSV, JSON, or XML) into a standardized tabular structure, apply domain-specific heuristics to infer missing data points, and annotate variables with relevant metadata.

The reasoner model 125 may operate by leveraging structured metadata, domain-specific rules, and artificial intelligence-driven inference to determine statistical analysis and visualization dynamically based on user queries.

The model 125 may initially parse a natural language query (e.g., from user device 150) to extract parameters, such as the type of clinical endpoint, relevant population subsets, and the desired comparison or outcome measure. In some cases, the query may be enriched, e.g., by substituting or adding synonyms, or inserting context based on session state, user profiles, or the like. In some cases, stop words or other terms may be filtered from the query. In some cases, the transformed query may be transformed into a vector in an embedding space in which distance corresponds to semantic similarity, such as one with more than 100 or more than 200 dimensions, with visualizations in index 130 being similarly characterized by such vectors for proximity-based matching.

Based on that vector, keywords, or other logic (e.g., implemented by a LLM or hard coded rules), the model 1255 may then traverse an indexed knowledge graph or other data structure that associates datasets, variables, statistical methods, and regulatory-approved visualization types to identify an appropriate analysis, such as the visualization index 130. A combination of LLM inference and rule-based logic may be used to evaluate contextual constraints, such as interrogating data in the visualization index 130 to ensure that only clinically validated, context suitable methodologies are recommended. For instance, if a query pertains to survival outcomes, the model may recognize that a Kaplan-Meier plot is suitable and confirm the presence of time-to-event variables within the dataset. In another example, when processing a query, the model 125 may interrogate the visualization index 130 to identify visualizations that align with the query parameters and metadata of the stored data. For instance, the index may indicate that a plot requires "time-to-event" and "event status" variables, guiding the reasoner model 125 to validate the availability of these variables before generating the visualization.

The reasoner model 125 may construct a query to index 130 to retrieve relevant visualizations by first parsing a natural language user query to extract structured parameters related to the requested analysis. The extracted parameters may then be mapped to corresponding metadata fields stored in a visualization index, which may maintain structured records of available visualizations along with their associated data requirements, statistical methodologies, and regulatory compliance attributes. In some cases, the mapping is based on semantic similarity search using proximity between embedding vectors (like those discussed above) for parsed query terms and terms in an ontology for describing visualizations in index 130, e.g., the closest terms in the ontology to the terms in the user query may be selected for forming the query to the index 130.

To generate the query to the index 130, the model 125 may apply a combination of template-based query generation and dynamic rule-based refinement. Initially, model 125 may construct a query skeleton by matching recognized entities in the user query to predefined metadata fields in the visualization index. For example, if the user query specifies "compare survival rates between treatment groups," the model may map "survival rates" to a time-to-event analysis category and "treatment groups" to a grouping variable, forming an initial query structure. The model may then refine the query using a combination of ontological reasoning and constraint checking, ensuring that the query aligns with available visualizations (or other forms of analysis) that support the specified analysis type. Model 125 may interrogate indexed metadata attributes such as required input variables, statistical assumptions, and regulatory-compliant formatting rules.

The constructed query may be formulated in a structured query language such as Structured Query Language (SQL), JsonPath query, XPATH, or a graph query language such as SPARQL, depending on the storage format of the visualization index 130. For example, in a relational database system, the query may involve filtering available visualizations by matching extracted parameters with corresponding database fields. If the visualization index is stored as a knowledge graph, the model may generate a graph traversal query to retrieve visualizations linked to the identified statistical method and data constraints. The model may further apply ranking heuristics to prioritize visualizations based on relevance, ensuring that the most contextually appropriate option is retrieved. Once the query to index 130 is executed, the model may validate the retrieved visualizations against dataset availability, refining the selection to ensure that the necessary input variables exist within the study data. The model 125 may further enforce parameter constraints, ensuring that only visualizations conforming to standards set by regulatory agencies such as the U.S. Food and Drug Administration (FDA) or the European Medicines Agency (EMA) are suggested.

The final visualization recommendations may then be selected (e.g., selecting the top 1, 3, 5 or more or less visualizations or other forms of analysis), and in some cases, those visualizations may be configured according to the parameters described in their metadata by dynamically adjusting graphical properties, data mappings, and computational transformations based on structured attributes stored in a visualization index. Each selected visualization may be associated with metadata that defines required input variables, statistical assumptions, axis labels, color schemes, aggregation methods, and formatting constraints. When a visualization is selected, the system 110 may retrieve its corresponding metadata and apply parameterized configurations to ensure compatibility with the underlying dataset and analytical requirements. For example, if a visualization metadata entry specifies that it requires a time-to-event variable and a grouping factor, the system may automatically identify and assign appropriate dataset columns to these roles, ensuring that survival curves or hazard ratios are correctly computed and displayed. The metadata may also define constraints on data types and statistical methods, preventing configurations that are incompatible with the visualization's intended analytical purpose.

Graphical properties such as axis scaling, tick mark intervals, legend placement, and color encoding may be adjusted dynamically based on metadata-driven rules. If a visualization supports logarithmic scaling, the system 110 may determine whether the data range justifies its application and configure the axes accordingly. Similarly, categorical variables may be mapped to discrete color palettes, while continuous variables may be assigned gradient-based color scales, with metadata specifying recommended schemes for consistency across analyses. Metadata may also define labeling conventions, ensuring that axis titles, legend descriptions, and annotation formats adhere to regulatory or domain-specific reporting standards.

Upon selecting and configuring a suitable analysis, the reasoner model 125 may construct a computational workflow dynamically, assembling operations for data filtering, transformation, and statistical calculations in real time. Rather than relying on precomputed outputs, the model may retrieve relevant data from repository 115, apply necessary transformations, and generate the selected visualizations (or other forms of analysis) dynamically based on the user-specified parameters. The model 125 may also support iterative refinement, allowing users to modify filters or redefine subgroups and receive updated results interactively.

In cases where visualizations require preprocessing steps such as data aggregation, normalization, or statistical transformation, the metadata may specify the required computations and their dependencies. For instance, if a box plot requires grouped summary statistics, the system may generate median, quartile, and outlier calculations before rendering the visualization. If a bar chart requires weighted means, the metadata may indicate the appropriate weighting variable, ensuring accurate representation of stratified or adjusted values. Additionally, metadata-driven configuration may extend to interactivity settings, such as whether tooltips, zooming, filtering, or drill-down capabilities should be enabled based on the intended use case.

When multiple visualizations are presented together, metadata may be used to enforce consistency in style and data presentation. Alignment of axis ranges across related charts, harmonization of color assignments for categorical groups, and synchronization of filtering parameters across linked visualizations may be determined using shared metadata attributes. These configurations may ensure that visual representations remain interpretable, comparable, and aligned with analytical expectations, allowing users to derive insights efficiently without manual adjustment.

In some embodiments, the visualization index 130 may store metadata, such as mappings, for visualizations supported by the server system 110. In some embodiments, the visualization index 130 may maintain a catalog of visualization types such as, bar charts, line graphs, scatter plots, histograms, swimmer plots, waterfall charts, forest plots, bubble charts, heatmaps, box plots, density plots, timeline charts, Gantt charts, hierarchical visualizations such as treemaps and sunburst charts, network visualizations such as chord diagrams and Sankey diagrams, geospatial maps, survival analyses, correlation matrices, and interactive dashboards. It should be appreciated that this list of visualization types is exemplary and not exhaustive (which is not to imply other lists are exhaustive), as additional visualizations may be included based on the specific requirements of the data or analytical workflows. In some embodiments, the visualization index 130 may store metadata requirements for a respective visualization to be generated. These metadata requirements may be stored alongside each visualization in the index. For each visualization, the index may describe the variables required for generation, applicable data structures, and configurable parameters such as axes or filters. In some embodiments, the visualization index 130 may store long-form descriptions of stored visualizations. These long-form descriptions may provide detailed explanations of the visualization's purpose, statistical methodologies, and underlying data processing techniques. The descriptions may include information regarding the type of statistical models or transformations applied to the dataset to generate the visualization. In some embodiments, the long-form description may include a detailed explanation of the visualization method itself, outlining the specific techniques used to construct the graphical representation. The long-form descriptions may assist in the visualization selection process by serving as metadata that can be analyzed for relevance when responding to a user query. When a query is received, the system may compare the query parameters to the contents of the long-form descriptions to determine whether the visualizations are appropriate for the requested analysis. Additionally, the long-form descriptions may be leveraged to enhance interpretability by providing users with supplementary contextual information about how the visualization was generated and what insights it is designed to convey. In some embodiments, when a user selects a visualization, the long-form description may be displayed alongside it, allowing the user to understand the analytical rationale behind the visualization.

The term visualization is used broadly to also include tabular forms of statistical analysis, such as the following examples. An analysis of variance table may present variance decomposition, including sums of squares, mean squares, F-statistics, and p-values for different factors in an ANOVA test. A regression coefficients table may summarize estimated coefficients, standard errors, t-values, and p-values in a regression model. A confusion matrix may display actual versus predicted classifications in machine learning or diagnostic testing, including true positives, false positives, true negatives, and false negatives. A descriptive statistics table may provide summary measures such as mean, median, standard deviation, minimum, and maximum for one or more variables. A correlation matrix may present correlation coefficients between multiple variables, often used in exploratory data analysis. A contingency table, also referred to as a crosstab, may show the frequency distribution of categorical variables, such as a two-by-two table for chi-square tests. A likelihood ratio test table may compare model fit statistics, often used in logistic regression or mixed-effects modeling. A survival analysis table may include a summary of survival times, hazard ratios, confidence intervals, and p-values from models such as Cox proportional hazards regression. A hypothesis test summary table may provide structured output listing test statistics, degrees of freedom, and p-values for statistical tests such as t-tests, chi-square tests, or Wilcoxon rank-sum tests. A variance-covariance matrix may display variances along the diagonal and covariances between variables in off-diagonal elements, used in regression modeling and factor analysis. A principal component loadings table may provide factor loadings in principal component analysis or factor analysis, showing the contribution of each variable to extracted components. A model fit statistics table may summarize metrics such as Akaike Information Criterion, Bayesian Information Criterion, R-squared, and log-likelihood for comparing statistical models. These types of statistical analyses may provide structured numerical outputs that support inference, model evaluation, or decision-making without necessarily requiring graphical visualization.

In some embodiments, visualizations (e.g., instructions on how to form the same, their requirements, and descriptions of their uses, without storing generated instances of such visualizations displaying clinical data in the index 130) may be stored in the visualization index 130, where each visualization is associated with metadata describing its characteristics, purpose, and requirements for generation. For example, visualizations may include metadata fields such as the dataset class, visualization name, description, component, and required mappings. The following code snippet illustrates how one embodiment may store visualizations in the visualization index:

```
get_visualizations("tall_longi")
[
        {
        "dataset_class": "tall_longi",
        "name": "Time Series Plots",
        "description": "Plot of longitudinal numeric data",
        "component": "LongiNumView",
        "required_mappings": {
        "tall": ["val_var", "param_var"],
        "tall_longi": ["visit_var", "visit_num_var"]
            }
        }
]
```

In this example, the visualization is associated with the dataset_class "tall_longi," indicating that it is applicable to datasets conforming to this class. The name field specifies the visualization type as "Time Series Plots," while the description provides additional context, describing the visualization as a plot of longitudinal numeric data. The component field identifies the specific visualization component, in this case, "LongiNumView," which may define the rendering logic or library used to generate the visualization.

The required_mappings field specifies the metadata requirements necessary to generate the visualization. For example, the required mappings for the "tall" dataset class include variables such as "val_var" and "param_var," while the "tall_longi" dataset class requires mappings for "visit_var" and "visit_num_var." These mappings support the system in validating the availability of required variables in the underlying dataset before attempting to generate the visualization. In some embodiments, additional metadata fields may be included to describe optional parameters, applicable filters, or recommended configurations for the visualization. In some cases, these values may be used to select candidate visualizations, and the reasoner model 125 may evaluate whether the selected candidates are suitable based on other fields beyond those used to select candidates with a query to index 130.

Some embodiments of server system 110 may include a view generator configured to dynamically generate the selected visualizations based on the corresponding clinical trial data in repository 115, and deliver responses back to the user device 150, e.g., in real-time, like within 2 minutes or less of a query, such as less than 500 ms. The user device 150 may present a user interface (such as one created with instructions sent by server system 110) that also allows users to refine their queries, apply filters, or adjust visualization parameters such as axes, color coding, or data subsets. For example, a user may submit a query requesting a Kaplan-Meier survival curve and subsequently refine the results to focus on a specific subpopulation by adjusting inclusion criteria on the user device 150. This refinement may be implemented by the user device 150 supplying a prompt to the server system 110 with the server system analyzing the prompt and providing the refinement or by the user device 150 utilizing refinement tools provided to it on the user interface, with the refinement tools allowing a user to apply filters, adjust visualization parameters, or additional refinement. Furthermore, the user device 150 (e.g., using this UI) may facilitate collaborative interactions, such as adding annotations to visualizations, sharing insights with team members, or exporting results for regulatory submission.

These visualizations may also be distributed to downstream systems, such as automated regulatory reporting platforms, collaborative research tools, or decision-support systems.

In some embodiments, the security and compliance layer 140 may assist the server system 110 in adhering to regulatory requirements and protects sensitive clinical trial data. This layer may implement role-based access control to restrict access to data and analyses based on user roles, such as administrators, clinicians, or data analysts. In some embodiments, the security and compliance layer 140 may also include data masking or anonymization techniques to protect patient privacy while supporting analysis of de-identified data. Additionally, the security and compliance layer 140 may maintain audit logs of all system interactions, including data access, transformations, and query executions, facilitating traceability for regulatory audits. Encryption protocols, such as TLS for data in transit and AES for data at rest, may be implemented to further safeguard data integrity and confidentiality.

In some embodiments, the security and compliance layer 140 may implement local encryption and anonymization techniques, while the server system 110 handles role-based access control and audit logging. Layer 140 may further enhance security by implementing authentication mechanisms, such as multi-factor authentication (MFA) or token-based access.

In some embodiments, the anomaly detection module 145 may identify unusual patterns, inconsistencies, or potential errors in the clinical trial data. In some embodiments, this module may employ machine learning algorithms to detect anomalies, such as data entry errors, fraudulent records, or deviations from expected distributions. For example, the module may flag adverse event reports that exceed statistically normal frequencies for a particular treatment arm, prompting further investigation. The anomaly detection module 145 may also support query-driven anomaly detection, allowing users to specify criteria for identifying anomalies in specific datasets or analyses. Additionally, the module may integrate with the security and compliance layer 140 to notify administrators of potential data integrity concerns.

In some embodiments, the anomaly detection module 145 may leverage an LLM, a computer vision model, or a multi-modal model to detect anomalies or inconsistencies in the generated visualizations. For example, a computer vision model (like a convolutional neural network or a vision transformer) may analyze the visualization along with its underlying data to identify potential issues, such as unexpected patterns, data points that deviate from trends, or inconsistencies between variables. This detection process may occur either in response to a specific user query or automatically during or after the visualization generation process. For instance, if a visualization highlights adverse event rates for multiple treatment arms, the vision model may detect and inform the user of an unusually high frequency of adverse events in a specific arm during a particular phase of the trial.

In some embodiments, an LLM may communicate these findings to the user through textual annotations or visual markers integrated directly into the visualization. For example, the system may display a message stating, "Adverse events for Treatment Group A exceed the expected range during Week 6. Click here for additional details." Alternatively, a diffusion model may highlight the relevant portion of the visualization, such as by circling a cluster of data points or applying a distinctive color to the anomalous region, drawing the user's attention to the potential issue. This functionality may be designed to operate proactively, offering unprompted insights or responding to user prompts for anomaly detection. Anomalies identified by these models may be seamlessly integrated into the system's issue tracking mechanism, allowing users to flag and document issues, initiate investigations, and apply corrective actions.

Figure 2:
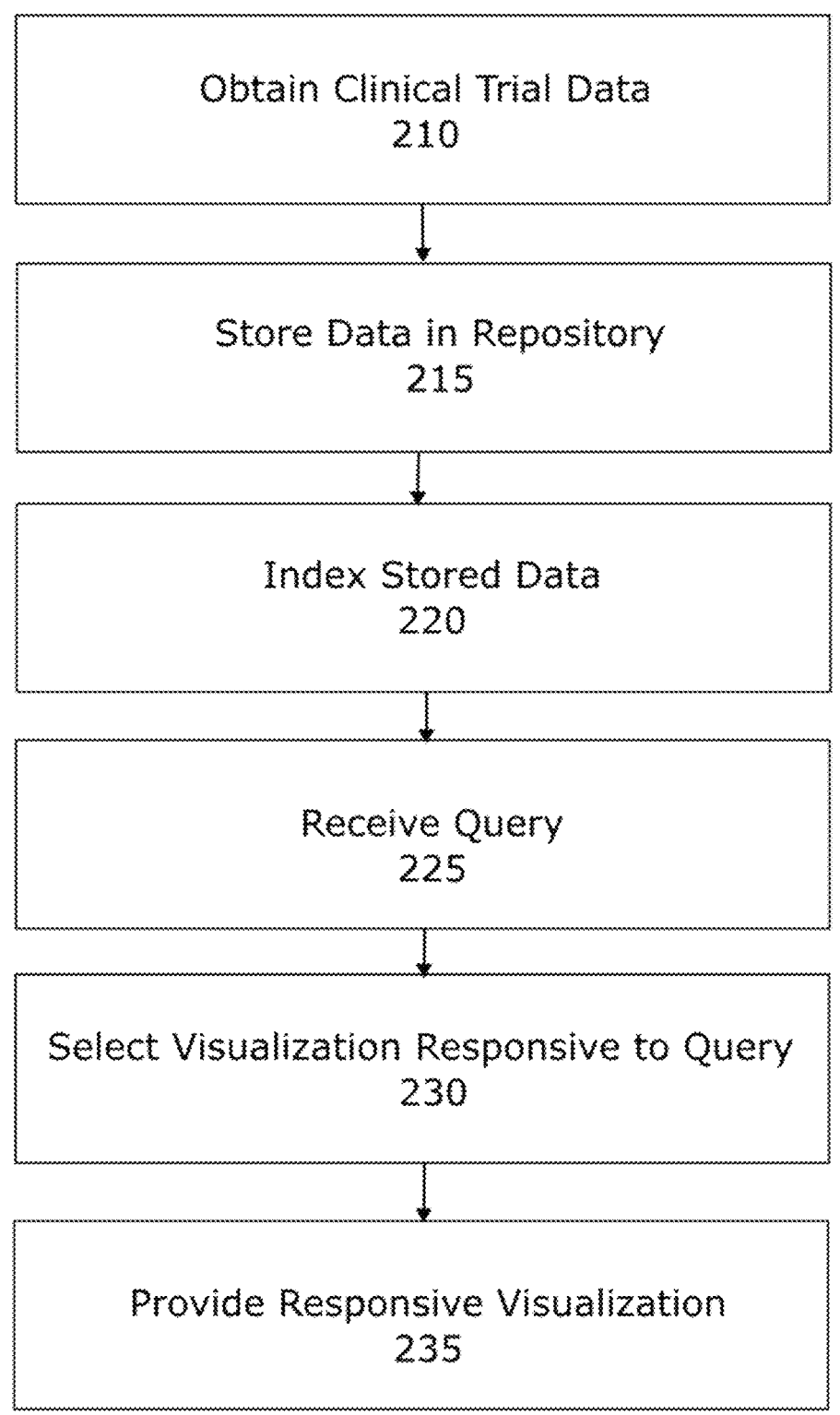
FIG. 2 illustrates a flowchart outlining the steps of an exemplary method for dynamically generating visualizations based on clinical trial data.

FIG. 2 illustrates a flowchart detailing steps of a process that may be used for dynamically generating visualizations and analyses based on clinical trial data. In some cases, this process may be performed by the system 110 described above or by other computing architectures.

The process of FIG. 2 may begin with obtaining clinical trial data 210, wherein the data may be sourced from publicly available clinical trial data repositories, private repositories, or other means of acquisition.

Once obtained, the data may be stored in a data repository 215, which may segment the data based on its source, type, format, or schema. In some embodiments, all data may be stored in a singular repository, while in others, the data may be distributed across multiple repositories based on logical or geographic segmentation. The repository may also employ a hierarchical or graph-based structure to link related datasets, such as linking patient records to associated laboratory results, treatment outcomes, and adverse event reports.

Once the data has been stored and transformed, some embodiments may include indexing the data stored in the data repository 115. This indexing process may involve associating the stored data and any performed analyses with metadata to facilitate efficient retrieval and support downstream analytical workflows. As part of the transformation process, the system may use mappings to convert diverse input formats into a unified data model. These mappings may define relationships between raw data attributes and standardized schema elements, allowing the system to integrate datasets originating from different formats, schemas, or modalities. For example, mappings may link a variable labeled "DOB" in one dataset to a "date_of_birth" field in the unified schema or associate a variable labeled "AE_Severity" with an "adverse_event_severity" field. The mappings may also account for transformations such as unit conversions, format standardizations, and inferred relationships between variables.

In some embodiments, mappings may be dynamically generated or refined based on metadata associated with the input data. Metadata may describe the structure, content, and relationships within a dataset, such as data types, column names, or hierarchical dependencies. During the indexing process, this metadata may be augmented with additional descriptors, such as lineage information, timestamps, or user annotations. The indexed metadata may not only facilitate traceability but also play a critical role in identifying relevant datasets and verifying that the transformed data aligns with analytical requirements.

Once the data has been successfully stored and transformed, some embodiments may include indexing the data 220 stored in the data repository 115. Additionally, analyses performed upon the data, whether before, during, or after ingestion, may also be indexed. Indexing may involve associating the stored data and any performed analyses with metadata that may encompass a wide range of criteria, attributes, or descriptors to facilitate querying and visualization. Examples of metadata may include the time and location of data capture, data ingestion timestamps, data schema details, descriptions of performed analyses, transformation history, relationships between datasets, and lineage information. Metadata may also include annotations, quality metrics, and mappings between dataset variables. The system may employ a versioned metadata store to support the traceability and reproducibility of data and analyses. For example, metadata may indicate the parameters used in a statistical analysis or describe the relationships between variables in a dataset, such as "age" and "adverse event severity."

The process may also include receiving a query 225 related to the stored clinical trial data. Queries may be submitted from a user device 150, other computer processes, or other sources, such as external systems or automated workflows. Queries may be expressed in various forms, such as natural language, Boolean logic, or other formats. For example, a query may ask, "Show adverse events by treatment arm," or specify logical conditions such as "age >60 AND adverse events=true." The server system 110 may process these queries, e.g., using a LLM to interpret their meaning, extract relevant entities and intents, and map them to applicable datasets or analyses. Alternative methods for query interpretation may include rule-based natural language processing engines, statistical parsers, or context-aware models trained on clinical trial data. Additionally, the system may allow users to refine or expand their queries interactively, using a feedback mechanism to provide more specific results.

In some embodiments, the system may be configured to pre-generate queries related to the stored clinical trial data. These pre-generated queries may be based on a variety of factors, such as previous user queries, user behavior, or pre-defined queries tailored to specific datasets. For instance, if a user previously queried "Adverse events by age group," the system may suggest related queries, such as "Adverse events by gender" or "Adverse events over time." Similarly, pre-defined queries may be generated based on metadata associated with the datasets, such as identifying frequently accessed variables or analyses of regulatory interest. This pre-generation capability may enhance the user experience by providing query suggestions, reducing the effort required to formulate complex queries, and guiding users toward insightful analyses. The system may also dynamically update pre-generated queries as new data is ingested or as query patterns evolve over time.

The system may then select one or more visualizations responsive to the query 230. These visualizations may be stored in a visualization index 130 described above, which may catalog predefined visualization templates and their metadata requirements. Metadata requirements for each visualization may describe the variables, data structures, and configurable parameters necessary for their generation. For example, a scatter plot may require two numeric variables, while a bar chart may require one categorical variable and one numeric variable. The process may include validating whether the metadata requirements of the visualizations align with the stored data before selecting a visualization. This validation step may occur before any recommendations are made or after initial recommendations have been suggested. For instance, the process of FIG. 2 may recommend visualizations but subsequently determine that some visualizations cannot be generated due to missing metadata, such as a "time-to-event" variable needed for a timeline chart.

The process of FIG. 2 may utilize a reasoner model to determine the most appropriate visualizations for a given query, as described above. In some embodiment, the process may employ other methods to select visualizations. For example, a rule-based selection engine may apply predefined criteria or heuristics to recommend visualizations based on query parameters and dataset characteristics. Metadata filtering may be used to directly match query requirements with the metadata of stored visualizations, bypassing the need for complex reasoning. In some implementations, a statistical or ensemble model may rank visualizations based on predicted relevance to the query. Collaborative filtering techniques may prioritize visualizations that were historically preferred for similar queries, while ontology-based matching may use predefined relationships between data domains and visualization types to recommend appropriate outputs. Additionally, some embodiments may present users with an interactive interface to manually select or refine visualizations from a list of applicable options.

In some embodiments, the process may dynamically generate executable code configured to generate the selected visualizations. This generation may occur in real time based on the query and associated metadata. The system may output the generated executable code in formats such as YAML (yet another markup language) or JSON (JavaScript object notation). Some embodiments may output code in a YAML format for generating human-readable scripts that define visualization configurations or workflows in a structured format, making it easier for users or downstream systems to interpret and modify. Some embodiments may use JSON format for machine-readable scripts that define parameters, data mappings, or API payloads, facilitating seamless integration with other systems or services. In some embodiments, the system may also support the generation of other types of executable code, such as Python™ scripts for data transformation and rendering or JavaScript™ for embedding interactive visualizations into web applications.

Some embodiments may adapt or customize predefined visualization templates by retrieving or modifying existing code to suit the specific parameters of the query. For example, the process may insert specific variable mappings or user-defined filters into a pre-written script, dynamically tailoring the visualization logic. In some configurations, the process may retrieve and execute pre-existing code from a library of scripts stored in the visualization index 130 to reduce computational time. Code generation may also be supported by machine learning models or external LLMs that dynamically create or refine the logic required to generate visualizations.

The generated executable code may then be executed to produce the visualizations responsive to the query. Execution may occur in the server system 110 or in alternative environments, such as the user device 150, or a distributed computing framework. In some cases, the system may transmit the generated code to an external system or device for execution. For example, visualizations may be rendered on a user interface hosted on the user device 150 or within a cloud-based analytics platform. The execution environment may be selected dynamically based on computational resource availability, proximity to the query source, or other operational considerations.

Once the visualizations have been generated, some embodiments may include providing the responsive visualizations 235 to the entity or system that submitted the query, such as a user device 150, or a downstream application. The process of FIG. 2 may transmit the visualizations in various formats, such as static images, interactive visualizations embedded in a user interface, or raw data exports that downstream systems can further process. In some embodiments, the visualizations may be embedded within a web-based dashboard or mobile application, allowing users to interact with the data directly by applying filters, adjusting axes, or drilling down into specific subsets. Alternatively, or additionally, the system may deliver the visualizations as part of an API response, supporting integration with third-party analytics tools or automated workflows. In some configurations, the visualizations may be provided as part of a report, formatted for regulatory submission or collaborative review. For example, the system may generate a PDF report that includes the visualizations alongside metadata annotations, descriptive summaries, or audit logs. Some embodiments may also provide the visualizations in a streaming format for real-time display in environments such as monitoring dashboards or decision-support systems.

In some embodiments, the process of FIG. 2 may leverage a LLM to interpret generated visualizations and provide users with written summaries, insights, or analyses. The LLM may analyze the visualized data, its underlying structure, and contextual metadata to identify patterns, trends, or anomalies. For example, after generating a scatter plot of patient response rates by treatment arm, the LLM may summarize key findings, such as, "Patients in Treatment Arm B exhibited a 25% higher response rate than those in Treatment Arm A." Additionally, the LLM may highlight specific outliers in the visualization, explaining their potential significance, such as "This data point indicates a patient with an unusually high response rate, which may warrant further investigation due to deviations from the overall trend."

In some configurations, the LLM may provide insights into previously hidden or unknown relationships within the data. For instance, it may identify correlations between variables not explicitly requested in the query or point out data clusters that suggest the presence of subpopulations. These findings may be presented as a list of key points or annotations integrated directly into the visualization or as a separate written report. For visualizations containing significant anomalies, the LLM may offer reasoning or context behind the anomalies, such as, "This spike in adverse events corresponds to a protocol change in Week 6." By analyzing and contextualizing the visualization, the LLM may offer users actionable insights, enhance the interpretability of complex datasets, and assist in uncovering patterns that might otherwise go unnoticed. This functionality may operate in response to user prompts or as an automatic feature, providing unprompted but relevant observations about the visualized data.

In some embodiments, the process may provide a toolset that allows users to manipulate, revise, or refine the generated visualizations. This toolset may be hosted on the user device 150, or another platform and may allow users to adjust visualization parameters, apply filters, or customize visual elements such as axes, color coding, or labels. For example, a user may modify a bar chart to filter specific treatment arms or adjust the time range displayed in a timeline chart. The toolset may also support collaborative features, such as adding annotations, sharing visualizations with team members, or exporting results for regulatory submissions. The tools may be accessible through an intuitive graphical user interface or exposed via APIs for integration with external systems.

Some embodiments implement a software-as-a-service (SaaS) interactive platform for clinical trial data analysis, referred to as Telperian Foundation™ (or "Foundation"). In some embodiments, the platform may provide a self-service interface that allows users, such as researchers and clinicians, to explore clinical trial data interactively. This interactive capability may allow users to identify insights and answer questions by navigating, querying, and visualizing their data directly through a client computing device communicating with a server system over a network.

In some embodiments, the platform described by FIGS. 1 and 2 above may be designed to support clients with diverse data sources and varying clinical trial workflows. Many existing Electronic Data Capture (EDC) systems may lack the scalability or adaptability required to provide interactive services for large numbers of users or to accommodate the variety of data formats encountered across trials. Some embodiments address these challenges by offering tools and techniques that organize clinical trial data in ways that support meaningful analysis without requiring significant manual preprocessing by users.

Some embodiments may structure clinical trial data to facilitate dynamic interaction, query-based exploration, and visualization. This structure may support a variety of analyses, such as safety monitoring, efficacy evaluation, and trend identification, while verifying the system remains adaptable to differing user needs and data scenarios. The system, in some embodiments, may utilize metadata, indexing, and other computational approaches to streamline data access and enhance the user experience, facilitating responsive interactions even with complex datasets.

Some embodiments may offer a suite of features designed to streamline and enhance the analytical process for researchers and clinicians by providing intuitive tools for exploring clinical trial data. These tools may include user-friendly interfaces that support natural language querying, interactive visualizations, and dynamic filtering of datasets. Through these capabilities, users may efficiently access relevant information without requiring extensive technical expertise or reliance on custom scripts, which may lower barriers to data exploration and interpretation.

In some embodiments, the system may reduce latency by employing optimized indexing and retrieval techniques, allowing users to quickly obtain query results and generate visualizations, even when working with large or complex datasets. Techniques such as distributed processing, in-memory data stores, and caching may be used to accelerate computational tasks. Computational efficiency may also be improved through advanced data compression, including lossless compression techniques, precomputed indices for high-frequency queries, and parallelized data processing across multiple servers or nodes.

These tools may support a wide range of analytical goals, offering flexibility for users to customize operations. Users may generate tailored visualizations, such as time-series plots, cohort comparisons, or multi-dimensional heatmaps, based on specific research objectives. For example, users might explore relationships between patient demographics and treatment efficacy, analyze trends in adverse events across treatment groups, or assess the impact of co-morbidities on clinical outcomes. Advanced filtering options and parameterized analysis features may allow users to refine queries, drill into subsets of data, and interactively adjust criteria to extract actionable insights.

The system may also assist in identifying patterns and trends across trials, contributing to faster and more effective clinical research workflows. Comparative analyses of efficacy and safety metrics across multiple studies or treatment arms may reveal early signals of promising therapies. Similarly, visualizing temporal trends in adverse events could support proactive safety monitoring and timely interventions. These interactive tools may further promote collaboration by allowing stakeholders to share datasets, annotate findings, and review analyses within a unified platform.

In some embodiments, systems may process and represent raw clinical trial data originating from multiple trials, with each dataset potentially structured in diverse formats and schemas. This variability may arise due to differences in trial design, data collection methodologies, and organizational preferences. For example, data from one trial may include electronic case report forms (CRFs) with structured demographic information, while another may incorporate laboratory results in semi-structured formats or unstructured text. Some embodiments may accommodate both consistent data structures across trials and heterogeneous datasets with varied schemas and formats.

Clinical trial data often requires precise handling of both data formats and schemas. A data format defines how data is physically represented and transmitted, such as JSON (JavaScript Object Notation), XML (Extensible Markup Language), or binary serialization formats like Protocol Buffers. Formats govern syntax and encoding but do not impose constraints on the relationships or semantics of the data. Conversely, a data schema provides a logical blueprint of data organization, defining attributes such as field names, data types, constraints, and relationships. Examples include database schemas written in Structured Query Language (SQL) or JSON Schema, which may validate the structure of JSON-formatted data.

Some embodiments may leverage both formats and schemas to validate, process, and enhance clinical trial data. While formats facilitate interoperability and low-level readability, schemas define the higher-level relationships and constraints that are critical for analysis. For instance, a schema may specify that an "age" field must be an integer within a valid range, while a format makes certain that the data is transmitted in a structured, parsable manner. These systems may validate the integrity of data assets by facilitating adherence to defined schemas while allowing flexibility in input formats, thereby supporting effective data integration and analysis.

By combining data format and schema management, systems may create an environment where diverse datasets can be indexed and analyzed efficiently. In some embodiments, metadata and indexing techniques may supplement this process, associating context, quality metrics, and other descriptors with datasets to enhance searchability and visualization. For example, metadata may describe the origin, type, and transformation history of data, supporting users in querying and navigating datasets seamlessly, regardless of their original structure or format.

Some embodiments may implement these present techniques using an object-oriented programming approach, where classes are instantiated to represent different datasets. Each dataset class in these embodiments includes a defined set of "mappings." These mappings may be generated through a multi-step, semi-automated process designed to associate variables within datasets to analytical or visualization concepts. In some embodiments, this process begins with an automated step where the system analyzes raw input datasets to infer their domains and classes. Algorithms may scan the data for indicators such as variable names, file naming conventions, and structural patterns expected for specific dataset types. For example, datasets conforming to CDISC standards, such as ADaM (Analysis Data Model) or SD™ (Study Data Tabulation Model), may be identified by detecting standard file name patterns, such as the inclusion of "aeds" in adverse events datasets, or by recognizing common variable names and structures associated with these standards.

In cases where datasets do not adhere to standard formats, the algorithms may rely on predictive techniques, such as machine learning models, to analyze variable naming conventions, statistical distributions, or metadata attributes. These models may assign confidence levels to the inferred domains and classes, and datasets with lower confidence scores may be flagged for further review.

Once the initial domain and class assignments are made, the system may present these results to the user through an interactive interface. This interface may allow domain experts or analysts to review, confirm, or modify the automated assignments. For instance, a dataset automatically classified as containing pharmacokinetic data based on its variable names might be reclassified as demographic data after further inspection by the user. Following user confirmation, the system may proceed to generate default mappings for the variables within each dataset. These mappings associate raw dataset variables-such as "age," "adverse event severity," or "treatment arm"—with predefined schema attributes or analytical concepts. The process may utilize rule-based logic, templates, or probabilistic methods to establish these mappings. For instance, a variable labeled "age" may be mapped to a numeric demographic attribute, while "severity" may be linked to a categorical attribute in a safety dataset.

In some embodiments, the system may identify variables for which mappings cannot be determined automatically and present these to the user for manual input. This may assist in making sure that ambiguous or non-standard variables are properly addressed. The system may also record user modifications and feedback to refine future mapping predictions, creating a continuous improvement loop that enhances the accuracy and efficiency of the process over time.

The resulting mappings may include metadata describing the variable's type, format, and transformation history, enhancing traceability and usability. For example, metadata may specify whether a variable is categorical or numeric, its allowable value range, or any transformations applied during preprocessing. This additional context may support downstream workflows such as querying, visualization, and analytical operations, verifying that the data is prepared consistently and accurately for a variety of use cases.

Some embodiments may support searches against visualizations, allowing users to query and retrieve visual representations of data directly from a dataset. These searches may be conducted using natural language queries, Boolean expressions, or other structured formats, allowing users to express their analytical needs intuitively. For example, a user might enter a query such as "show adverse events by treatment arm and age group" or "compare efficacy across study sites," and the system may process this input to identify and generate relevant visualizations.

In some embodiments, the system may employ indexing techniques to associate pre-generated visualizations with potential queries. These visualizations may be prepared during data ingestion or analysis and indexed with metadata describing their content, such as variables, filters, and applied conditions. For instance, a bar chart comparing adverse event rates by treatment arm may be indexed with keywords like "adverse events," "treatment arm," and "comparison."

Some embodiments may dynamically generate visualizations at query time. In this approach, the system may parse the user's query to identify relevant datasets, variables, and conditions, and then construct a visualization based on these parameters. For example, in response to a query such as "plot age distribution for treatment group A," the system may extract the specified data, apply any necessary transformations, and render an appropriate visualization (e.g., a histogram) in real-time.

To facilitate these capabilities, some embodiments may leverage advanced query parsing and visualization frameworks. Natural language processing (NLP) models may interpret user queries, extracting key entities (e.g., variables, conditions, or comparison metrics) and mapping them to corresponding data elements within the system. For instance, an NLP model may recognize "age distribution" as a request for a frequency distribution and "treatment group A" as a filter condition. Similarly, Boolean expressions or structured query inputs may be directly parsed into machine-executable instructions for visualization generation.

Some embodiments may employ LLMs, including multimodal LLMs, to pre-generate query lists that are associated with visualizations prior to query execution. These models may analyze the metadata, content, and variables linked to each visualization to produce a comprehensive set of possible queries that a user might input to retrieve that visualization. For example, metadata describing a visualization of "adverse events by treatment arm" may lead an LLM to generate queries such as "What are the adverse event rates across treatment arms?", "Compare adverse events for drug A and drug B," or "Show a breakdown of adverse events by treatment groups."

Some embodiments may present the LLM with prompts that include structured metadata and examples of the variables and content in the visualization to support this capability. The prompts may specify key relationships or constraints, guiding the model to generate meaningful, domain-specific queries. For instance, a visualization that shows a time-series of efficacy results may have associated metadata indicating variables such as "efficacy rate," "time point," and "treatment arm." The LLM, using this metadata, may generate queries such as "Plot efficacy over time for all treatment arms" or "How does treatment efficacy change over time for placebo vs. active drug groups?"

Some embodiments may index any generated queries to support efficient and fast query-response workflows. The index may link each visualization to its associated queries and their metadata, creating a structure optimized for rapid matching during query execution. For example, the index may store metadata tags, query strings, and a mapping to the corresponding visualizations. When a user submits a query, the system may compare the input against the indexed query list to identify matches. In some cases, indexed queries may be normalized to account for variations in phrasing or language, such as recognizing "Show adverse events by treatment arm" as equivalent to "Compare adverse events across treatment arms."

Matching user queries to indexed queries may involve several techniques to facilitate robust and accurate retrieval. In some embodiments, keyword-based matching may be applied, where the system evaluates the co-occurrence of query terms with metadata tags associated with the indexed queries. For instance, a query including the keywords "adverse events" and "treatment" may be matched to indexed queries with similar terms. This approach may leverage metrics such as term frequency-inverse document frequency (TF-IDF) scores to rank potential matches based on relevance.

Alternatively, or in addition, the system may employ semantic similarity techniques using vector embedding spaces. In this approach, both user queries and indexed queries may be represented as high-dimensional vectors, with the similarity between them determined by their proximity in the embedding space. This technique may utilize pre-trained or fine-tuned embedding models, such as transformer-based architectures, to capture semantic nuances and context within the queries. For example, a user query like "Break down safety outcomes by drug arm" may be interpreted as semantically similar to indexed queries about "adverse events" and "treatment groups," even if the exact wording differs. The system may rank potential matches based on their similarity scores, selecting the highest-ranking visualization for retrieval.

In addition to query interpretation, some embodiments may incorporate ranking mechanisms to prioritize and present the most relevant visualizations to users. Relevance metrics may consider factors such as data quality, recency, and similarity to prior queries. For instance, a query returning multiple potential visualizations may rank those visualizations by their alignment with the user's intent, as determined through metadata and query context.

Some embodiments may also integrate interactive elements into the visualizations, allowing users to refine their queries or adjust parameters directly within the interface. For example, a user viewing a line graph of efficacy trends over time may apply filters, adjust axes, or switch to a different visualization type (e.g., bar chart or scatter plot) without needing to re-enter the query.

Some embodiments include the following features, which may be implemented server-side in a software as a service distributed architecture communicating with a client computing device or as a monolithic application executing locally on a client computing device:

Some embodiments may manage digital entities in clinical trials, including patient records, treatment regimens, adverse event reports, pharmacokinetic profiles, diagnostic data, and analytical outputs. These entities, in some embodiments, may include metadata providing context, such as the origin, capture time, source device, and any preprocessing applied. In some embodiments, these entities may be represented using structured data formats, such as JSON or XML, to facilitate interoperability across systems. In some cases, a globally unique identifier (GUID) may be assigned to each digital entity, allowing cross-referencing across datasets. In some embodiments, hierarchical relationships may be established among digital entities, linking, for example, a patient record to associated laboratory results or adverse event logs. In some embodiments, these entities may be represented within a blockchain-based structure to facilitate data immutability or within a graph database to model complex relationships, such as associations between treatment regimens, patient demographics, and outcomes.

Some embodiments may include an issue tracking mechanism to monitor and resolve anomalies, inconsistencies, or observations in clinical trial data. The system may, in some embodiments, allow users to flag specific data points, visualizations, or analytical results, categorizing flagged issues as errors, observations, or questions. Each issue may be linked to the relevant data or visualization, enhancing traceability and contextual awareness. In some embodiments, metadata such as severity, timestamps, and user identifiers may be associated with issues, and collaborative features, such as user mentions, may be implemented to facilitate resolution. In some cases, automated issue detection may identify anomalies, such as missing values, statistical outliers, or unexpected distributions, and flag these for review. Some embodiments may integrate issue tracking with version control systems, allowing users to track the evolution of flagged issues across dataset versions and resolve issues in bulk where appropriate.

The issue tracking mechanism described herein may be implemented in a manner consistent with the techniques disclosed in U.S. Non-Provisional patent application Ser. No. 18/990,773, the specification of which is hereby incorporated by reference in its entirety for all purposes. By integrating issue detection and tracking into multiple stages of the data handling process, the system may enhance reliability, traceability, and compliance for clinical trial data management.

In some embodiments, notifications may be employed to alert stakeholders to data anomalies, procedural updates, or critical analytical results. Notifications may be sent via multiple channels, including email, SMS, or push notifications within a web or mobile application. Triggering conditions may include thresholds for adverse events, ingestion of new data, or the creation of high-severity flagged issues. Role-based notifications may verify that stakeholders, such as researchers, clinicians, and data analysts, receive only the information pertinent to their responsibilities. In some embodiments, notification preferences may be customizable, allowing users to define thresholds or select preferred delivery methods. Notifications, in some embodiments, may include links to visualizations or data points to provide immediate context. Additional embodiments may involve integrating notifications with external collaboration platforms, such as Slack or Microsoft Teams, to support workflows across multiple tools.

Some embodiments may provide an asset versioning mechanism to track changes and updates to digital entities within clinical trial datasets. The system, in some embodiments, may maintain a full history of modifications, allowing users to revert to prior versions or compare differences between versions. For example, differences between dataset versions may highlight newly added adverse events or updates to demographic attributes. In some cases, cryptographic hash pointers may be employed to link versions, providing tamper-evident properties and facilitating data integrity. Batch processing functionality may allow for the resolution or annotation of updates across an entire dataset version. Some embodiments may also present dashboards detailing changes or time-series visualizations to summarize changes across dataset versions. In other embodiments, the system may support the automatic generation of comparison reports detailing key modifications.

Some embodiments may include a search and logging module to enhance the retrieval and traceability of clinical trial data. The search functionality may support natural language queries, Boolean operators, and advanced filters, allowing users to locate specific records, analyses, or visualizations efficiently. For example, a query such as "Show adverse events for patients aged 65+ in Treatment Group A" may dynamically retrieve relevant results. The logging module, in some embodiments, may maintain an immutable, time-stamped record of system interactions, including data edits, query submissions, and issue resolutions. Logs may be associated with metadata, such as user IDs, action types, and affected datasets, facilitating a complete audit trail for regulatory compliance. Some embodiments may incorporate faceted search to group results by attributes such as trial phase or treatment arm, while others may implement real-time search indexing to provide immediate access to newly ingested data.

Some embodiments may verify the reliability and authenticity of clinical trial data through layers of validation, security, and traceability. Validation workflows may automatically detect inconsistencies, such as unrealistic age values or duplicate patient records, and flag them for review. Role-based access control, in some embodiments, may restrict data modifications to authorized users, with all changes logged for transparency. Some embodiments may employ cryptographic techniques, such as digital signatures or hash-linked data structures, to verify tamper-evident properties. In other cases, redundancy and replication may be used to prevent data loss by storing datasets across geographically distributed servers. To further support reliability, some embodiments may include real-time monitoring and anomaly detection systems, with automatic notifications for potential data integrity concerns. Additional permutations may involve machine learning-based anomaly detection or blockchain-based systems to secure data provenance.

A reasoner model, such as model 125 described above, may be configured to analyze a given query, evaluate relevant metadata and dataset characteristics, and determine an optimal response based on predefined rules, probabilistic inference, or machine learning techniques. In some embodiments, the reasoner model may operate as a decision-making engine that maps input queries to applicable datasets, analyses, and visualizations by leveraging structured rules, metadata associations, and learned representations. The model may process user queries in various forms, such as natural language, Boolean logic, or structured query languages, and translate them into structured instructions that define which datasets should be accessed, what transformations should be applied, and which visualizations may be most relevant.

The reasoner model may utilize multiple stages of processing to interpret queries and derive meaningful insights. Initially, the model may apply natural language processing (NLP) techniques, such as tokenization, named entity recognition (NER), and dependency parsing, to extract key entities and intents from a query. For example, a query such as "Show treatment response trends over time for patients aged 65 and older" may be parsed to identify the relevant variables ("treatment response," "time"), conditions ("patients aged 65 and older"), and the appropriate visualization type (e.g., a line graph). The reasoner model may then retrieve metadata from indexed datasets and visualizations to determine whether the requested variables exist and whether they satisfy the requirements for generating an appropriate response.

Once the relevant datasets and metadata have been identified, the reasoner model may apply logical inference rules to refine query execution. This may involve mapping query elements to structured data fields, verifying constraints (e.g., facilitating a valid cohort exists within the dataset), and resolving ambiguities by ranking potential data sources based on relevance. In some implementations, the reasoner model may incorporate domain-specific ontologies or hierarchical taxonomies to improve the accuracy of query interpretation and dataset selection. For instance, if a user submits a vague query such as "Compare patient outcomes," the reasoner model may infer that "outcomes" could refer to survival rates, adverse events, or efficacy scores and prompt the user for clarification.

In some embodiments, the reasoner model may utilize a rule-based system to interpret queries and determine applicable datasets and visualizations. A rule-based reasoner may operate using a predefined set of logical conditions, mappings, and heuristics that associate query components with metadata attributes. For example, if a query contains the phrase "compare treatment arms," the rule-based system may recognize this as a request for categorical analysis and automatically select a bar chart or forest plot. Rule-based reasoning may also incorporate domain-specific ontologies that define relationships between clinical concepts, allowing the system to infer correct data mappings and refine ambiguous queries. While rule-based models offer transparency and interpretability, they may require extensive manual curation and may struggle with novel queries that do not match predefined rules.

Some embodiments may implement a probabilistic inference model that assigns likelihood scores to different query interpretations and selects the most probable response. Probabilistic models may incorporate Bayesian networks, Markov models, or other statistical frameworks to infer query intent based on observed metadata distributions. For example, given a query such as "show survival trends," a probabilistic model may evaluate metadata associated with stored datasets and determine the likelihood that time-series analysis or survival modeling is appropriate. The model may then recommend visualizations accordingly, adjusting its confidence based on prior query-response interactions.

In some implementations, the reasoner model may utilize machine learning techniques to improve query interpretation and visualization selection. Supervised learning models may be trained using historical query logs, mapping user queries to datasets and visualization types based on labeled training data. These models may include decision trees, support vector machines, or neural networks that classify queries and predict relevant visualizations. Additionally, deep learning architectures such as transformer-based models may analyze the semantic structure of queries, identifying implicit relationships between query components and metadata attributes. By continuously updating model parameters based on user feedback, machine learning-based reasoners may improve over time, adapting to new query patterns and evolving user needs.

In some embodiments, the system may utilize a reinforcement learning strategy to select one or more visualizations as being responsive to a query. This reinforcement learning strategy may allow the system to optimize visualization selection over time by continuously refining decision-making based on query metadata, visualization attributes, and user interactions. The reinforcement learning strategy may involve defining a policy model configured to map metadata associated with each visualization and the received query to a probability distribution over candidate visualizations. The policy model may leverage machine learning techniques, such as neural networks, decision trees, or probabilistic graphical models, to determine the likelihood that a given visualization is the most appropriate response to the query.

To improve visualization selection accuracy, some embodiments may define a reward function configured to assign a reward value to each candidate visualization. The reward function may incorporate multiple criteria to evaluate candidate visualizations, including relevance to the query, readability, accuracy, and alignment with user preferences. Relevance of a visualization may be determined based on semantic alignment between the metadata associated with the visualization and the query. For example, if a query requests a time-series trend, the system may prioritize visualizations that include temporal data, such as line graphs or time-series plots. Readability of a visualization may be determined based on compliance with predefined formatting and stylistic standards, verifying that visualizations are easily interpretable by users. Accuracy of the visualization may be determined by validating visualization consistency with the underlying data, such as checking for data integrity, facilitating proper scaling, and verifying that visualized values match the indexed dataset. Alignment with user preferences may be determined based on explicit feedback, such as user ratings or selections, or implicit behavioral signals, such as repeated interactions with certain visualization types.

Training the policy model using reinforcement learning may involve generating a plurality of candidate visualizations for a set of queries, evaluating each candidate visualization using the reward function to calculate reward values, and optimizing the policy model based on the calculated reward values. Candidate visualizations may be generated using different visualization techniques, layout configurations, or data representations, allowing the policy model to learn patterns of visualization relevance and appropriateness. The system may then evaluate each visualization according to the reward function, computing a numerical reward score that reflects the visualization's effectiveness in conveying the requested information. The policy model may be updated iteratively using techniques such as policy gradient optimization, Q-learning, or actor-critic methods to improve the probability of selecting candidate visualizations with higher reward values.

In some embodiments, the system may pre-select a subset of candidate visualizations before applying reinforcement learning by filtering visualizations based on metadata criteria such as visualization type, data source, or dimensionality. For example, if a query involves categorical comparisons, the system may prioritize bar charts, histograms, or heatmaps over line graphs or scatter plots. This pre-selection step may reduce computational complexity while verifying that reinforcement learning is applied only to visualizations with relevant data mappings.

During training, the system may balance exploration and exploitation to improve generalization across diverse queries and metadata configurations. Exploration may involve testing new visualization strategies or recommending visualizations that have not been frequently selected, whereas exploitation may involve selecting historically high-reward visualizations that have demonstrated effectiveness for similar queries. This balance may allow the policy model to continuously improve and adapt to changing data distributions and user preferences.

At inference time, the system may dynamically adjust the policy model based on real-time user feedback or changes in query or metadata distributions. For example, if a user frequently refines a visualization by adjusting parameters or selecting alternative layouts, the system may adapt the policy model to incorporate these refinements into future visualization selections. Similarly, if the underlying dataset evolves with new data or schema modifications, the system may update its visualization mappings to support continued alignment with the available data.

Selecting one or more visualizations responsive to the query may involve calculating an expected reward for each candidate visualization based on the metadata and query parameters. The system may rank the candidate visualizations according to their expected reward scores and select the visualization(s) with the highest scores as being the most appropriate response to the query. In some embodiments, the system may present multiple visualization options to the user, allowing for manual selection while still leveraging reinforcement learning to guide the ranking process. Additionally, the integration of user feedback and real-time adjustments may allow the system to refine its recommendations continuously, verifying that selected visualizations align with both user preferences and the evolving nature of the underlying clinical trial data.

The reinforcement learning approach may be implemented using techniques such as Group Relative Policy Optimization (GRPO), as described in DeepSeek-R1-Zero, where training is performed through iterative reinforcement learning without relying on supervised fine-tuning. The policy model may improve reasoning capabilities through self-evolution, learning from historical query-response interactions, and adjusting selection criteria dynamically. The model may generate and evaluate multiple candidate visualizations, ranking them based on expected reward scores, and optimizing future selections through reinforcement feedback loops.

The reasoning models described herein may be implemented in a manner consistent with the techniques disclosed in DeepSeek-RI: Incentivizing Reasoning Capability in LLMs via Reinforcement Learning (DeepSeek-AI), arXiv: 2501.12948, which is hereby incorporated by reference in its entirety for all purposes. This incorporation supports the disclosure of reinforcement learning methodologies applied to reasoning tasks, visualization selection, and dynamic data interpretation.

The reasoner model may also coordinate the selection of visualizations based on metadata attributes and predefined constraints. For example, if a selected dataset includes time-series data, the reasoner model may prioritize time-based visualizations such as line graphs or Kaplan-Meier curves. If categorical comparisons are requested, it may recommend bar charts or heatmaps. In some embodiments, the reasoner model may evaluate visualization constraints dynamically, verifying that selected visualizations align with available data structures and metadata requirements.

After determining the most appropriate datasets, analyses, and visualizations, the reasoner model may generate a structured execution plan that defines the steps required to retrieve and process the data. This plan may specify data transformations, statistical operations, and visualization parameters necessary to construct a response. The system may then execute this plan, generate the required output, and present the results to the user. In some cases, the reasoner model may also provide explanatory text or recommendations to help users interpret the results, such as highlighting trends, flagging potential anomalies, or suggesting alternative visualizations for deeper analysis.

SaaS Architecture

Some embodiments may be implemented within a Software as a Service (Saas) architecture, leveraging distributed cloud infrastructure for scalability, reliability, and flexibility. The physical architecture of the system, in some embodiments, may utilize cloud service providers such as AWS (Amazon Web Services), Google Cloud, Microsoft Azure, or similar platforms. These cloud environments may support the deployment of web servers, application servers, and database servers, allowing the system to accommodate varying levels of demand while maintaining high availability. In some configurations, load balancers may be employed to distribute incoming application traffic across multiple servers, preventing bottlenecks and facilitating consistent response times. Storage systems may feature multi-tiered options, with fast-access solid-state drives (SSDs) handling frequently accessed datasets and archival storage systems, such as hard drives or object storage solutions, preserving historical data for long-term retention. In some embodiments, backup and disaster recovery subsystems may be implemented to protect data integrity, with regular backups stored in geographically separate locations to safeguard against data loss or corruption.

Network security, in some embodiments, may be achieved through a combination of firewalls, virtual private clouds (VPCs), and encryption protocols. Firewalls may protect the internal network from unauthorized access or external threats, while VPCs may isolate resources within a secure, private environment. Data in transit may be encrypted using transport layer security (TLS), facilitating confidentiality and integrity during transmission. Data at rest may undergo encryption using symmetric or asymmetric encryption protocols, with encryption keys managed securely using hardware security modules (HSMs) or cloud-based key management services. Additional security measures, such as intrusion detection systems (IDS) and automated threat response mechanisms, may also be integrated to enhance the system's security posture.

Some embodiments may incorporate monitoring and logging tools for real-time system visibility and alerting. These tools may include solutions such as Amazon CloudWatch, ELK Stack, Datadog, or their equivalents. Monitoring systems may track performance metrics, such as server utilization, query response times, and user activity, while logging systems may record events such as data access, configuration changes, and error occurrences. Real-time alerting mechanisms may notify administrators of anomalies or threshold breaches, supporting prompt resolution of issues.

The logical architecture of the system, in some embodiments, may include a user interface (UI) layer, which may feature a web-based interface for researchers, clinicians, and data analysts to interact with clinical trial data. This interface may support operations such as querying datasets, generating visualizations, and annotating findings. In other embodiments, a mobile interface may extend similar functionalities to mobile devices, allowing users to access the platform remotely. Additionally, some embodiments may include application programming interface (API) endpoints to facilitate integration with third-party applications or systems, supporting seamless data exchange and interoperability.

An application layer may handle various functionalities such as authentication and authorization, business logic, and analytics. Authentication and authorization mechanisms may include OAuth, single sign-on (SSO), or other security protocols to control user access. Business logic may govern operations such as data validation, transformation, and reporting. Advanced analytics and reporting tools may provide features like cohort analysis, trend visualization, and statistical modeling, with support for exporting results to formats like PDF or CSV for offline use.

In some embodiments, the data access layer may utilize database management systems (DBMS) such as relational databases (e.g., PostgreSQL, MySQL) or non-relational databases (e.g., MongoDB, Cassandra). Object-Relational Mapping (ORM) tools, such as Hibernate or Sequelize, may facilitate database operations by abstracting query logic and managing schema evolution. This layer may also support indexing and caching mechanisms to optimize query performance, especially for large-scale datasets.

The data layer of the system, in some embodiments, may store clinical trial data, including patient records, laboratory results, adverse event reports, and efficacy metrics. Metadata describing the origin, capture time, and transformation history of the data may be stored alongside the primary data to enhance traceability. Audit logs may record modifications and access events, facilitating compliance with regulatory requirements and supporting detailed tracking of data usage.

Integration capabilities, in some embodiments, may allow the system to connect with external systems, such as clinical trial management systems, laboratory information systems, and electronic health records (EHRs). Data import and export functionalities may support interoperability, with configurable adapters to handle different data formats or protocols. Integration with external APIs or standards such as HL7 or FHIR may further enhance connectivity.

A security and compliance layer may verify adherence to standards such as HIPAA (Health Insurance Portability and Accountability Act) and GDPR (General Data Protection Regulation). Role-Based Access Control (RBAC) may define user permissions, restricting data access based on user roles and responsibilities. In some embodiments, data masking and anonymization features may be applied to protect sensitive patient information while allowing analysis of de-identified data.

An operations and maintenance layer may include tools for automated testing, continuous integration, and deployment (CI/CD). These tools may validate system functionality, security, and performance, verifying that updates and improvements are deployed reliably. Scripts and testing frameworks may simulate user activity or data workflows to identify potential issues before production deployment.

Some embodiments may include additional features to enhance functionality, such as real-time collaboration tools, predictive modeling for trial outcomes, and AI-driven analytics modules for anomaly detection or trend prediction. Voice recognition for data input, virtual assistants for guiding users, and automated alerts for emerging data patterns may also be implemented to provide a more intuitive and efficient user experience.

Search Techniques

Some embodiments may implement search functionality over data assets using a variety of Information Retrieval (IR) models, allowing users to efficiently locate and analyze relevant documents, visualizations, or data points. In some embodiments, the system may employ Classical IR models, which allow users to input structured Boolean expressions to refine their searches. For example, a user might input queries such as "Adverse Events AND Treatment Group A" or "Efficacy NOT Placebo," prompting the system to retrieve data entries or documents that meet the specified criteria. To enhance the precision of such queries, some embodiments may support advanced Boolean operators, proximity matching, and wildcard searches to capture complex relationships within the data.

In addition to Boolean logic, some embodiments may use vector-based representations for both user queries and documents. In these systems, textual data and queries may be encoded as high-dimensional vectors in a Vector Space Model (VSM). The system may calculate the similarity between a query vector and document vectors using metrics such as cosine similarity or Euclidean distance. The vector-based approach may support both Binary VSM for exact matches and Weighted Non-Binary VSM for relevance-based ranking. This methodology may support ranking of search results, prioritizing documents or data entries that align closely with the query's intent.

Further, some embodiments may treat documents or data entries as distributions of terms and compare the similarity of term distributions to assess relevance. In such cases, the system may calculate metrics such as entropy, divergence, or utility scores to rank results. For example, a query related to "adverse events" may prioritize documents with a higher concentration of terms such as "severity," "frequency," and "duration" if those terms are semantically linked to the query.

In other embodiments, the system may implement Non-Classical IR models, which may rely on propositional logic or other advanced paradigms to interpret complex queries. For instance, users may define intricate conditions, such as "Show all patients who reported severe adverse events within 30 days of treatment initiation AND belong to Treatment Group B." The system may parse and execute such queries, evaluating the logical relationships to identify and retrieve relevant data assets. In some embodiments, the system may enhance result relevance by incorporating context-aware processing, such as using user profiles, historical behavior, or session context to refine query interpretation. For example, a user who frequently queries demographic data may receive higher-ranked results related to demographic variables when issuing ambiguous queries.

Some embodiments may employ Alternative IR models to enhance search capabilities, particularly when dealing with large or unstructured datasets. For example, the system may group similar data assets into clusters using clustering algorithms. Upon executing a search, the system may identify the most relevant cluster(s) and retrieve data assets within those clusters, reducing search scope and improving efficiency. Clustering techniques, such as k-means or hierarchical clustering, may organize data assets based on similarity metrics derived from metadata, term distributions, or vector embeddings.

Other embodiments may employ Latent Semantic Indexing (LSI), which analyzes relationships between terms to uncover hidden semantic structures within the data. By identifying patterns of term co-occurrence, LSI may provide results that capture the underlying meaning of a query, even when exact terms are not matched. For example, a query like "Drug efficacy comparison" may retrieve documents related to "treatment outcomes" or "response rates," as these concepts may be semantically aligned. Additionally, some embodiments may utilize the Fuzzy Set model to handle imprecise or ambiguous queries. This approach may allow approximate matches, verifying that queries with typographical errors or vague phrasing still return relevant results. Generalized Vector Space Models (GVSMs) may also be employed, extending traditional VSMs by incorporating additional factors, such as metadata attributes or temporal dimensions, into vector representations to improve ranking accuracy.

Some embodiments may enhance search functionality with additional features. For example, voice search capabilities may allow users to dictate queries, which the system may process using speech-to-text and natural language understanding models. NLP may further improve query interpretation by identifying entities, extracting intent, and disambiguating terms. For instance, NLP techniques may recognize that "adverse events in elderly patients" refers to filtering adverse event data by age group. Multi-language support may allow global users to query the system in their native language, with real-time translation into the system's primary query language.

To improve relevance over time, some embodiments may incorporate machine learning models that learn from user interactions, query histories, and feedback. For example, if a user frequently selects certain types of documents or visualizations, the system may prioritize comparable results in future searches. The system may also include features like preferences for commonly accessed documents, verifying that high-priority assets appear prominently in search results. Some embodiments may integrate visualization tools, allowing users to explore search results graphically, such as through histograms, pie charts, or heatmaps, to identify patterns and insights more effectively.

Some embodiments may also support pre-indexing of data to expedite query responses. During this process, the system may create structured indices on frequently queried fields, such as subject identifiers, treatment arms, or event categories. These indices may support rapid lookups, facilitating low-latency responses even for large-scale datasets. In certain configurations, the system may combine pre-indexed data with real-time query execution for hybrid performance optimization. Additionally, dynamic indexing may allow the system to update indices as new data is ingested, verifying that all relevant information is accessible for queries without manual intervention.

Figure 3:
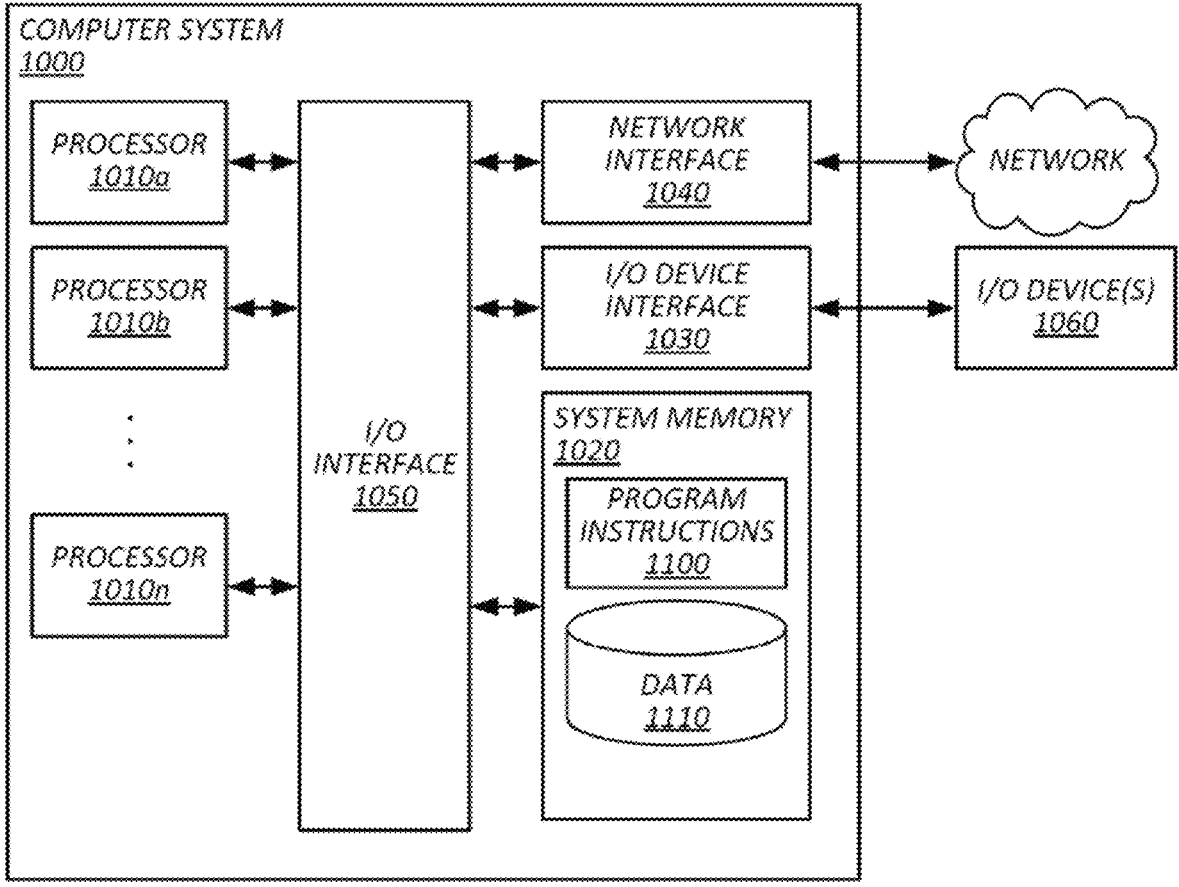
FIG. 3 illustrates a computer system configured to execute the method for dynamically generating visualizations and analyses based on clinical trial data.

FIG. 3 is a diagram that illustrates an exemplary computing system 1000 in accordance with embodiments of the present technique. A single computing device is shown, but some embodiments of a computer system may include multiple computing devices that communicate over a network, for instance in the course of collectively executing various parts of a distributed application. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010a-1010n) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010*a*), or a multi-processor system including any number of suitable processors (e.g., 1010*a*-1010*n*). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computer system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computer system 1000 through a wired or wireless connection. I/O devices 1060 may be connected to computer system 1000 from a remote location. I/O devices 1060 located on remote computer system, for example, may be connected to computer system 1000 via a network and network interface 1040.

Network interface 1040 may include a network adapter that provides for connection of computer system 1000 to a network. The network interface 1040 may facilitate data exchange between computer system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors 1010*a*-1010*n*) to implement one or more embodiments of the present techniques. Instructions 1100 may include modules of computer program instructions for implementing one or more techniques described herein with regard to various processing modules. Program instructions may include a computer program (which in Some forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine-readable storage device, a machine-readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors 1010*a*-1010*n*) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the complete set of instructions may be stored concurrently on the media, or in some cases, different parts of the instructions may be stored on the same media at different times.

I/O interface 1050 may be configured to coordinate I/O traffic between processors 1010*a*-1010*n*, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors 1010*a*-1010*n*). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 1000 or multiple computer systems 1000 configured to host different portions or instances of embodiments. Multiple computer systems 1000 may provide for parallel or sequential processing/execution of one or more portions of the techniques described herein.

Those skilled in the art will appreciate that computer system 1000 is merely illustrative and is not intended to limit the scope of the techniques described herein. Computer system 1000 may include any combination of devices or software that may perform or otherwise provide for the performance of the techniques described herein. For example, computer system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 1000 may also be connected to other devices that are not illustrated or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g., within a data center or geographically), or otherwise differently organized. The functionality described herein may be provided by one or more processors of one or more computers executing code stored on a tangible, non-transitory, machine-readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to cost constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and some features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include," "including," and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square," "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first," "second," "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A method, comprising: obtaining, with a computer system, data associated with clinical trials, wherein the data is sourced from a plurality of formats and modalities; storing, with the computer system, the obtained data into a repository by: preprocessing the data to standardize diverse input formats into unified data model; and organizing the stored data into a schema designed to integrate data of diverse input formats; indexing, with the computer system, the stored data and analyses performed on the stored data, wherein indexing comprises associating metadata with each analysis; receiving, with the computer system, a query related to the stored data; selecting, with the computer system, one or more visualizations responsive to the query by: selecting one or more visualizations as being responsive to the query based on metadata associated with each of the one or more visualizations; determining whether the stored data is associated with a plurality of metadata requirements of each of the one or more visualizations; dynamically generating executable code configured to generate the one or more visualizations responsive to the query, wherein the executable code is generated based on the query, metadata associated with the visualizations, and mappings between the metadata associated with the visualizations and the stored data; and executing the generated executable code; and providing, with the computer system, a response to the query, the response comprising the selected one or more visualizations.

2. The method of embodiment 1, wherein the selecting one or more visualizations as being responsive to the query comprises: utilizing, with the computer system, a reinforcement learning strategy to select the one or more visualizations, the reinforcement learning strategy comprising: defining, with the computer system, a policy model configured to map metadata associated with each visualization and the query to a probability distribution over candidate visualizations; defining, with the computer system, a reward function configured to assign a reward value to each candidate visualization, the reward value being assigned based on: relevance of the visualization to the query, wherein relevance is determined based on semantic alignment between the metadata and the query; readability of the visualization, wherein readability is determined based on compliance with predefined formatting and stylistic standards; accuracy of the visualization, wherein accuracy is determined by validating visualization consistency with underlying data; and alignment with user preferences, wherein user preferences are derived from explicit feedback or implicit behavioral signals; training, with the computer system, the policy model using reinforcement learning, the training comprising: generating a plurality of candidate visualizations for a set of queries; evaluating each candidate visualization using the reward function to calculate reward values; and optimizing the policy model based on the calculated reward values to improve the probability of selecting candidate visualizations with higher reward values; pre-selecting, with the computer system, a subset of candidate visualizations by applying metadata filtering criteria based on visualization type, data source, or dimensionality; balancing, with the computer system, exploration of diverse candidate visualizations and exploitation of historically high-reward candidates during training; dynamically adjusting, with the computer system, the policy model during inference based on real-time user feedback or changes in query or metadata distributions; and selecting, with the computer system, the one or more visualizations responsive to the query by: calculating, using the policy model, an expected reward for each candidate visualization based on the metadata and query; ranking the candidate visualizations based on their expected rewards; and selecting the one or more visualizations with the highest expected rewards as being responsive to the query.

3. The method of embodiment 1, wherein the query is expressed in at least one of natural language, Boolean expressions, or structured formats.

4. The method of embodiment 1, further comprising: providing, on a user interface, tools for interacting with the query response, wherein the tools comprise options to refine queries, annotate results, or collaborate with other users.

5. The method of embodiment 1, further comprising: maintaining an audit log of user queries, interactions, and data transformations.

6. The method of embodiment 1, wherein the data associated with clinical trials comprises at least one of patient records, laboratory results, adverse events, demographic data, or pharmacokinetic data.

7. The method of embodiment 1, further comprising: imputing missing data points in a stored dataset using algorithms implemented as modules within a distributed computing framework, the algorithms selected from statistical imputation methods, machine learning models trained on historical clinical trial data, or domain-specific heuristics, wherein imputed data is flagged with metadata containing a cryptographic hash to indicate the source and method of imputation.

8. The method of embodiment 1, wherein the metadata associated with indexed analyses is stored in a versioned metadata store and includes fields describing data transformations, analysis creation timestamps, data lineage, and cross-references to related datasets, wherein the metadata store is implemented as a graph database configured to facilitate traversal-based searches for visualizations and analyses related to the query.

9. The method of embodiment 1, wherein indexing comprises applying lossless compression techniques, wherein indexing is parallelized across multiple compute nodes.

10. The method of embodiment 1, wherein receiving a query comprises processing the query with a natural language processing engine implemented using a transformer-based deep learning model configured to extract entities, detect query intents, and translate the query into a structured format compatible with the indexed schema.

11. The method of embodiment 1, further comprising: dynamically updating the provided visualizations in real-time, wherein the updates include applying metadata-driven filters, adjusting visualization parameters such as axes and scales, and color-coding subsets of data based on user-defined or system-suggested criteria.

12. The method of embodiment 1, wherein the selected visualizations include multi-layered dashboards comprising integrated incidence plots, swimmer plots, and heatmaps, each visualization being generated using pre-defined mappings stored in a visualization index and rendered dynamically using a graph-based data representation linked to user-specific queries.

13. The method of embodiment 1, wherein ranking search results comprises evaluating relevance metrics, including data recency, analysis quality scores, similarity to historical user queries, and proximity to query terms in a vector embedding space, wherein the relevance metrics are computed using a weighted scoring algorithm.

14. The method of embodiment 1, further comprising: implementing role-based access control, wherein user roles are defined and permissible operations, such as query execution, data export, or visualization modification, are logged in an immutable audit trail.

15. The method of embodiment 1, wherein indexing comprises creating specialized indices for high-frequency queries by monitoring query patterns in real time, and precomputing search results for queries exceeding predefined thresholds of frequency and complexity.

16. The method of embodiment 1, further comprising: caching query results in a distributed in-memory data store, wherein cached results are indexed by query parameters and metadata, and subsequent matching queries retrieve the cached results.

17. The method of embodiment 1, wherein the provided visualizations are integrated into clinical decision support systems to assist in patient stratification, treatment planning, or safety monitoring.

18. The method of embodiment 1, wherein generating visualizations comprises passing the query to a large language model code generation engine, wherein the code generation engine returns executable code that, when executed, create a visualization responsive to the query, and wherein the visualization is rendered by executing the generated code on a local or cloud-based computing environment.

19. A tangible, non-transitory, machine-readable medium storing instructions that when executed by a data processing apparatus cause the data processing apparatus to perform operations comprising: the operations of any one of embodiments 1-18.

20. A system, comprising: one or more processors; and memory storing instructions that when executed by the processors cause the processors to effectuate operations comprising: the operations of any one of embodiments 1-18.

What is claimed is:
1. A method, comprising:
obtaining, with a computer system, data associated with clinical trials in a repository;
imputing missing data points in a stored dataset using algorithms implemented as modules within a distributed computing framework, the algorithms selected from statistical imputation methods, machine learning models trained on historical clinical trial data, or domain-specific heuristics, wherein imputed data is flagged with metadata containing a cryptographic hash to indicate a source and method of imputation;
obtaining, with the computer system, an index of visualizations, the index having metadata of the visualizations;
receiving, with the computer system, a query related to the obtained data;

selecting, with the computer system, one or more visualizations responsive to the query by:

selecting one or more visualizations as being responsive to the query based on the metadata associated with the visualizations, and determining whether the obtained data satisfies a plurality of metadata requirements of each of the one or more visualizations;

dynamically generating the selected one or more visualizations responsive to the query; and providing, with the computer system, a response to the query, the response comprising the generated one or more visualizations, wherein the metadata associated with indexed analyses is stored in a versioned metadata store and includes fields describing data transformations, analysis creation timestamps, data lineage, and cross-references to related datasets, wherein the metadata store is implemented as a graph database configured to facilitate traversal-based searches for visualizations and analyses related to the query.

2. The method of claim 1, wherein the selecting one or more visualizations as being responsive to the query comprises:

utilizing, with the computer system, reinforcement learning to select the one or more visualizations, the reinforcement learning comprising:

defining, with the computer system, a policy model configured to map metadata associated with each visualization and the query to a probability distribution over candidate visualizations;

defining, with the computer system, a reward function configured to assign a reward value to each candidate visualization, the reward value being assigned based on:

relevance of the visualization to the query, wherein relevance is determined based on semantic alignment between the metadata and the query;

readability of the visualization, wherein readability is determined based on compliance with predefined formatting and stylistic standards;

accuracy of the visualization, wherein accuracy is determined by validating visualization consistency with underlying data; and alignment with user preferences, wherein user preferences are derived from explicit feedback or implicit behavioral signals;

training, with the computer system, the policy model using reinforcement learning, the training comprising:

generating a plurality of candidate visualizations for a set of queries;

evaluating each candidate visualization using the reward function to calculate reward values; and optimizing the policy model based on the calculated reward values to improve the probability of selecting candidate visualizations with higher reward values;

pre-selecting, with the computer system, a subset of candidate visualizations by applying metadata filtering criteria based on visualization type, data source, or dimensionality;

balancing, with the computer system, exploration of diverse candidate visualizations and exploitation of historically high-reward candidates during training;

dynamically adjusting, with the computer system, the policy model during inference based on real-time user feedback or changes in query or metadata distributions; and selecting, with the computer system, the one or more visualizations responsive to the query by:

calculating, using the policy model, an expected reward for each candidate visualization based on the metadata and query;

ranking the candidate visualizations based on their expected rewards; and selecting the one or more visualizations with a highest expected reward as being responsive to the query.

3. The method of claim 1, wherein the query is expressed in at least one of natural language, Boolean expressions, or structured formats.

4. The method of claim 1, further comprising:

providing, on a user interface, tools for interacting with the query response, wherein the tools comprise options to refine queries, annotate results, or collaborate with other users.

5. The method of claim 1, further comprising:

maintaining an audit log of user queries, interactions, and data transformations.

6. The method of claim 1, wherein the data associated with clinical trials comprises at least one of patient records, laboratory results, adverse events, demographic data, or pharmacokinetic data.

7. The method of claim 1, further comprising indexing the obtained data in the repository, the indexing comprising applying lossless compression techniques, wherein the indexing is parallelized across multiple compute nodes.

8. The method of claim 1, wherein receiving a query comprises processing the query with a natural language processing engine implemented using a transformer-based deep learning model configured to extract entities, detect query intents, and translate the query into a structured format compatible with an indexed schema.

9. The method of claim 1, further comprising:

dynamically updating the provided visualizations in real-time, wherein the updates include applying metadata-driven filters, adjusting visualization parameters such as axes and scales, and color-coding subsets of data based on user-defined or system-suggested criteria.

10. The method of claim 1, wherein the selected visualizations include multi-layered dashboards comprising integrated incidence plots, swimmer plots, and heatmaps, each visualization being generated using pre-defined mappings stored in a visualization index and rendered dynamically using a graph-based data representation linked to user-specific queries.

11. The method of claim 1, further comprising:

searching the index of visualizations based on the query by encoding the query and metadata associated with stored visualizations as vectors in a vector space model; and ranking search results by evaluating relevance metrics, including data recency, analysis quality scores, similarity to historical user queries, and proximity to query terms in a vector embedding space, wherein the relevance metrics are computed using a weighted scoring algorithm.

12. The method of claim 1, further comprising:

implementing role-based access control, wherein user roles are defined and permissible operations, such as query execution, data export, or visualization modification, are logged in an immutable audit trail.

13. The method of claim 7, wherein indexing comprises creating specialized indices for high-frequency queries by monitoring query patterns in real time, and precomputing search results for queries exceeding predefined thresholds of frequency and complexity.

14. The method of claim 1, further comprising:

caching query results in a distributed in-memory data store, wherein cached results are indexed by query parameters and metadata, and subsequent matching queries retrieve the cached results.

15. The method of claim 1, wherein the provided visualizations are integrated into clinical decision support systems to assist in patient stratification, treatment planning, or safety monitoring.

16. The method of claim 1, wherein generating visualizations comprises passing the query to a large language model code generation engine, wherein the code generation engine returns executable code that, when executed, creates a visualization responsive to the query, and wherein the visualization is rendered by executing the generated code on a local or cloud-based computing environment.

17. The method of claim 1, wherein the method further comprises steps for selecting one or more visualizations using a reasoner model.

18. A tangible, non-transitory, machine-readable medium storing instructions that when executed by a data processing apparatus cause the data processing apparatus to perform operations comprising:

obtaining, with a computer system, data associated with clinical trials in a repository;

imputing missing data points in a stored dataset using algorithms implemented as modules within a distributed computing framework, the algorithms selected from statistical imputation methods, machine learning models trained on historical clinical trial data, or domain-specific heuristics, wherein imputed data is flagged with metadata containing a cryptographic hash to indicate a source and method of imputation;

obtaining, with the computer system, an index of visualizations, the index having metadata of the visualizations;

receiving, with the computer system, a query related to the obtained data;

selecting, with the computer system, one or more visualizations responsive to the query by:

selecting one or more visualizations as being responsive to the query based on the metadata associated with the visualizations, and determining whether the obtained data satisfies a plurality of metadata requirements of each of the one or more visualizations;

dynamically generating the selected one or more visualizations responsive to the query; and providing, with the computer system, a response to the query, the response comprising the generated one or more visualizations, wherein the metadata associated with indexed analyses is stored in a versioned metadata store and includes fields describing data transformations, analysis creation timestamps, data lineage, and cross-references to related datasets, wherein the metadata store is implemented as a graph database configured to facilitate traversal-based searches for visualizations and analyses related to the query.

19. A tangible, non-transitory, machine-readable medium storing instructions that when executed by a data processing apparatus cause the data processing apparatus to perform operations comprising:

obtaining, with a computer system, data associated with clinical trials, wherein the data is sourced from a plurality of formats and modalities;

storing, with the computer system, the obtained data into a repository by:

preprocessing the data to standardize diverse input formats into a unified data model; and organizing the stored data into a schema designed to integrate data of diverse input formats;

imputing missing data points in a stored dataset using algorithms implemented as modules within a distributed computing framework, the algorithms selected from statistical imputation methods, machine learning models trained on historical clinical trial data, or domain-specific heuristics, wherein imputed data is flagged with metadata containing a cryptographic hash to indicate a source and method of imputation;

indexing, with the computer system, the stored data and analyses performed on the stored data, wherein indexing comprises associating metadata with each analysis;

receiving, with the computer system, a query related to the stored data;

selecting, with the computer system, one or more visualizations responsive to the query by:

selecting one or more visualizations as being responsive to the query based on metadata associated with each of the one or more visualizations;

determining whether the stored data is associated with a plurality of metadata requirements of each of the one or more visualizations;

dynamically generating executable code configured to generate the one or more visualizations responsive to the query, wherein the executable code is generated based on the query, metadata associated with the visualizations, and mappings between the metadata associated with the visualizations and the stored data; and executing the generated executable code; and providing, with the computer system, a response to the query, the response comprising the selected one or more visualizations, wherein the metadata associated with indexed analyses is stored in a versioned metadata store and includes fields describing data transformations, analysis creation timestamps, data lineage, and cross-references to related datasets, wherein the metadata store is implemented as a graph database configured to facilitate traversal-based searches for visualizations and analyses related to the query.

20. The medium of claim 18, wherein the selecting one or more visualizations as being responsive to the query comprises:

utilizing, with the computer system, reinforcement learning to select the one or more visualizations, the reinforcement learning comprising:

defining, with the computer system, a policy model configured to map metadata associated with each visualization and the query to a probability distribution over candidate visualizations;

defining, with the computer system, a reward function configured to assign a reward value to each candidate visualization, the reward value being assigned based on:

relevance of the visualization to the query, wherein relevance is determined based on semantic alignment between the metadata and the query;

readability of the visualization, wherein readability is determined based on compliance with predefined formatting and stylistic standards;

accuracy of the visualization, wherein accuracy is determined by validating visualization consistency with underlying data; and alignment with user preferences, wherein user preferences are derived from explicit feedback or implicit behavioral signals;

training, with the computer system, the policy model using reinforcement learning, the training comprising:

generating a plurality of candidate visualizations for a set of queries;

evaluating each candidate visualization using the reward function to calculate reward values; and optimizing the policy model based on the calculated reward values to improve the probability of selecting candidate visualizations with higher reward values;

pre-selecting, with the computer system, a subset of candidate visualizations by applying metadata filtering criteria based on visualization type, data source, or dimensionality;

balancing, with the computer system, exploration of diverse candidate visualizations and exploitation of historically high-reward candidates during training;

dynamically adjusting, with the computer system, the policy model during inference based on real-time user feedback or changes in query or metadata distributions; and selecting, with the computer system, the one or more visualizations responsive to the query by:

calculating, using the policy model, an expected reward for each candidate visualization based on the metadata and query;

ranking the candidate visualizations based on their expected rewards; and selecting the one or more visualizations with a highest expected reward as being responsive to the query.

21. The medium of claim 18, the operations further comprising:

searching the index of visualizations based on the query by encoding the query and metadata associated with stored visualizations as vectors in a vector space model; and ranking search results by evaluating relevance metrics, including data recency, analysis quality scores, similarity to historical user queries, and proximity to query terms in a vector embedding space, wherein the relevance metrics are computed using a weighted scoring algorithm.

22. The medium of claim 18, the operations further comprising:

providing, on a user interface, tools for interacting with the query response, wherein the tools comprise options to refine queries, annotate results, or collaborate with other users.

23. The medium of claim 18, the operations further comprising:

maintaining an audit log of user queries, interactions, and data transformations.

24. The medium of claim 18, wherein the data associated with clinical trials comprises at least one of patient records, laboratory results, adverse events, demographic data, or pharmacokinetic data.

25. The medium of claim 18, the operations further comprising:

imputing missing data points in a stored dataset using algorithms implemented as modules within a distributed computing framework, the algorithms selected from statistical imputation methods, machine learning models trained on historical clinical trial data, or domain-specific heuristics, wherein imputed data is flagged with metadata containing a cryptographic hash to indicate a source and method of imputation.

26. The medium of claim 18, wherein the metadata associated with indexed visualizations is stored in a versioned metadata store and includes fields describing data transformations, analysis creation timestamps, data lineage, and cross-references to related datasets, wherein the metadata store is implemented as a graph database configured to facilitate traversal-based searches for visualizations and analyses related to the query.

27. The medium of claim 18, the operations further comprising indexing the obtained data in the repository, the indexing comprising applying lossless compression techniques, wherein the indexing is parallelized across multiple compute nodes.

28. The medium of claim 27, wherein indexing comprises creating specialized indices for high-frequency queries by monitoring query patterns in real time, and precomputing search results for queries exceeding predefined thresholds of frequency and complexity.

29. The medium of claim 18, the operations further comprising:

dynamically updating the provided visualizations in real-time, wherein the updates include applying metadata-driven filters, adjusting visualization parameters such as axes and scales, and color-coding subsets of data based on user-defined or system-suggested criteria.

30. The medium of claim 18, wherein the selected visualizations include multi-layered dashboards comprising integrated incidence plots, swimmer plots, and heatmaps, each visualization being generated using pre-defined mappings stored in a visualization index and rendered dynamically using a graph-based data representation linked to user-specific queries.

31. The medium of claim 18, wherein the query is expressed in at least one of natural language, Boolean expressions, or structured formats.

32. The medium of claim 18, the operations further comprising:

implementing role-based access control, wherein user roles are defined and permissible operations, such as query execution, data export, or visualization modification, are logged in an immutable audit trail.

33. The medium of claim 18, wherein receiving a query comprises processing the query with a natural language processing engine implemented using a transformer-based deep learning model configured to extract entities, detect query intents, and translate the query into a structured format compatible with an indexed schema.

34. The medium of claim 18, the operations further comprising:

caching query results in a distributed in-memory data store, wherein cached results are indexed by query parameters and metadata, and subsequent matching queries retrieve the cached results.

35. The medium of claim 18, wherein the provided visualizations are integrated into clinical decision support systems to assist in patient stratification, treatment planning, or safety monitoring.

36. The medium of claim 18, wherein generating visualizations comprises passing the query to a large language model code generation engine, wherein the code generation engine returns executable code that, when executed, creates a visualization responsive to the query, and wherein the visualization is rendered by executing the generated code on a local or cloud-based computing environment.

37. The medium of claim 18, the operations further comprising steps for selecting one or more visualizations using a reasoner model.

38. A method, comprising:

obtaining, with a computer system, data associated with clinical trials, wherein the data is sourced from a plurality of formats and modalities;

storing, with the computer system, the obtained data into a repository by:

preprocessing the data to standardize diverse input formats into a unified data model; and organizing the stored data into a schema designed to integrate data of diverse input formats;

imputing missing data points in a stored dataset using algorithms implemented as modules within a distributed computing framework, the algorithms selected from statistical imputation methods, machine learning models trained on historical clinical trial data, or domain-specific heuristics, wherein imputed data is flagged with metadata containing a cryptographic hash to indicate a source and method of imputation;

indexing, with the computer system, the stored data and analyses performed on the stored data, wherein indexing comprises associating metadata with each analysis;

receiving, with the computer system, a query related to the stored data;

selecting, with the computer system, one or more visualizations responsive to the query by:

selecting one or more visualizations as being responsive to the query based on metadata associated with each of the one or more visualizations;

determining whether the stored data is associated with a plurality of metadata requirements of each of the one or more visualizations;

dynamically generating executable code configured to generate the one or more visualizations responsive to the query, wherein the executable code is generated based on the query, metadata associated with the visualizations, and mappings between the metadata associated with the visualizations and the stored data; and executing the generated executable code; and providing, with the computer system, a response to the query, the response comprising the selected one or more visualizations, wherein the metadata associated with indexed analyses is stored in a versioned metadata store and includes fields describing data transformations, analysis creation timestamps, data lineage, and cross-references to related datasets, wherein the metadata store is implemented as a graph database configured to facilitate traversal-based searches for visualizations and analyses related to the query.

\* \* \* \* \*